(12) United States Patent
Bladh et al.

(10) Patent No.: US 7,030,246 B2
(45) Date of Patent: Apr. 18, 2006

(54) TETRAHYDROQUINOLINE DERIVATIVES AS STAT6-MODULATORS, PREPARATION AND USE THEREOF

(75) Inventors: Håkan Bladh, Lund (SE); Thomas Hansson, Lund (SE); Grigorios Nikitidis, Lund (SE); Carita Nordén, Lund (SE); Lars Pettersson, Lund (SE); Mikael Varga, Lund (SE)

(73) Assignee: Astrazeneca AB, Södertälje (SE)

( * ) Notice: Subject to any disclaimer, the term of this patent is extended or adjusted under 35 U.S.C. 154(b) by 51 days.

(21) Appl. No.: 10/473,056

(22) PCT Filed: Mar. 26, 2002

(86) PCT No.: PCT/SE02/00597

§ 371 (c)(1),
(2), (4) Date: Sep. 29, 2003

(87) PCT Pub. No.: WO02/079165

PCT Pub. Date: Oct. 10, 2002

(65) Prior Publication Data

US 2004/0132724 A1    Jul. 8, 2004

(30) Foreign Application Priority Data

Mar. 30, 2001   (SE) ................................... 0101161

(51) Int. Cl.
C07D 215/16    (2006.01)
C07D 215/20    (2006.01)
A61K 31/47     (2006.01)

(52) U.S. Cl. .................. 546/159; 546/157; 514/312
(58) Field of Classification Search ................ 514/312; 546/159, 157
See application file for complete search history.

(56) References Cited

FOREIGN PATENT DOCUMENTS

| EP | 1 283 055 | 2/2003 |
|---|---|---|
| JP | 2002-53557 | * 2/2002 |
| WO | WO 00/17165 | 3/2000 |
| WO | WO 00/17166 | 3/2000 |
| WO | WO 01/76629 | 10/2001 |

OTHER PUBLICATIONS

Chemical Abstracts 1974:403048, vol. 81 (1974) 3048e (copy of Russian paper also attached).
Chemical Abstracts 1968:427206, vol. 69 (1968) 27206h.
Chemical Abstracts 1967: 453250, vol. 67 (1967) 53250w (copy of Russian paper also attached).
L.P. Zalukaev, et al., HCAPLUS, Accession No. 1974: 403048, Document No. 81:3048, "Bimolecular alkylidene arylamines. XII. Catalysis as the disproportionation of homolyzation energy," (1974).
L.P. Zalukaev, et al., HCAPLUS, Accession No. 1968: 427206, document No. 69:27206, "Intramolecular donor-acceptor interaction in 2-7ethyl-4-anilino-1, 2, 3, 4-tetrahydroquinoline and its derivatives," (1968).
L.P. Zalukaev, et al., HCAPLUS, Accession No. 1967: 453250, Document No. 67:53250, "Bimolecular alkylidenearylamines. XI. New data on intermolecular donor-acceptor reactions in 4-anilino-2-methyl-1, 2, 3, 4-tetrahydroquinolines," (1967).
Derwent Abstract 2002-311644/35 (of JP 2002053557), English translation of the claims attached.
Chemical Abstracts, vol. 62, 1965:3908c-e.
Chemical Abstracts, vol. 10, 1957:1994e-h.
Chemical Abstracts, vol. 51, 1992d-f.
Chemical Abstracts, vol. 65, 1966:15179f.
Chemical Abstracts, vol. 51, 5076e-f.
José Barluenga, et al., "Catalytic and Non-catalytic Addition of Aromatic Amines to Terminal Acetylenes in the Presence of Mercury (II) Chloride and Acetate," Journal of the Chemical Society, Perkin Transections 1, vol. 12, pp. 2732-2737, (1980).
Masuo Funabashi, et al., "Configuration and Conformation of So-called Bis(alkylidenearylamines)," Bulletin of the Chemical Society of Japan, vol. 42, pp. 2885-2894 (1969).
Robert E. Harmon, et al, "Keten Imine-Dimethyl Sulphoxide Oxidation of 2',3'-o-Isopropylideneadenosine," Compound IV and V, Chemical Communications, vol. 119, p. 1969, (Feb. 3, 1969).
G.A. Dauphinee, et al, "1,2-Dihydroquinolines: preparation and isolation as intermediates in the synthesis of quinolines," Compound 3, Canadian Journal of Chemistry, vol. 56, No. 5, pp. 632-634, (1978).
Minoru Uchida, et al., "Synthesis and Antiulcer Activity of 4-substituted 8-[(2-Benzimidazolyl)sulfinylmethyl]-1,2,3,4-tetrahydroquinolines and Related Compounds, " IX a-e, chart 6, Chem. Pharm, Bull., vol. 38, No. 6, pp. 1575-1586 (1990).
Angelo Clerici, et al., "Arylative Amination of Aldehydes Promoted by Aqueous Titanium Trichloride," Compound 7, Tetrahedron Letters, vol. 31, No. 14, pp. 2069-2072 (1990).

* cited by examiner

Primary Examiner—D. Margaret Seaman
(74) Attorney, Agent, or Firm—Fish & Richardson P.C.

(57) ABSTRACT

Compounds of formula (I) are modulators of STAT6 signal pathway activity, and can be used in the treatment of atopic dermatitis, urticaria, allergic asthma, allergic rhinitis, a food allergy, allergic conjunctivitis, hayfever, bullous pemphigoid, industrial sensitization, chronic rejection of transplants or COPD

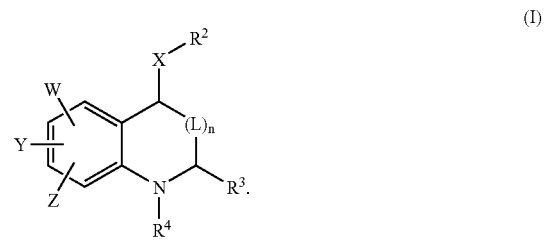

14 Claims, No Drawings

TETRAHYDROQUINOLINE DERIVATIVES AS STAT6-MODULATORS, PREPARATION AND USE THEREOF

The present invention relates to tetrahydroquinoline derivatives which are modulators of the Signal Transducer and Activator of Transcription 6 (STAT6) pathway, to processes for their preparation, to pharmaceutical compositions comprising them and to methods of using them (for example for the treatment of STAT6-mediated diseases).

STATs are proteins involved in signal transduction from cytokine and growth factor receptors. STAT6 binds to specific phosphotyrosine motifs on an activated IL4/IL-13 receptor α-chain. Once bound, the protein is phosphorylated by JAK kinases and then STAT6 forms a homodimer that translocates into the nucleus and stimulates gene transcription. Gene knockout studies in mice have shown that STAT6 is required for IL-4/IL-13 responses that have pathological consequences in allergic disease, namely IgE production and differentiation of T helper cells to the Th2 phenotype. (Linehan L A. Warren W D. Thompson P A. Grusby M J. Berton M T. STAT6 is required for IL4-induced germline Ig gene transcription and switch recombination. *Journal of Immunology.* 161(1):302–10, 1998; Kaplan M H. Schindler U. Smiley S T. Grusby M J. Stat6 is required for mediating responses to IL4 and for development of Th2 cells. *Immunity.* 4(3):313–9, 1996; Malabarba M G. Rui H. Deutsch C H. Chung J. Kalthoff F S. Farrar W L. Kirken R A. Interleukin-13 is a potent activator of JAK3 and STAT6 in cells expressing interleukin-2 receptor-gamma and interleukin-4 receptor-alpha. *Biochemical Journal.* 319 (Pt 3):865–72, 1996.)

Interference with STAT6 activation would be expected to reduce the production of proinflamatory cytokines like IL-4 and IL-5. A compound antagonizing STAT6 would, therefore, be expected to have utility in treating disease states such as asthma, dermatitis (allergic and atopic), urticaria, rhinitis and/or COPD.

1,2,3,4-Tetrahydroquinolines are disclosed in WO 00/17165 and WO 00/17166.

The present invention provides a compound of formula (I):

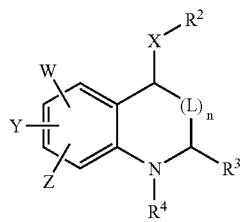

(I)

wherein:
L is $CH_2$, O or S;
n is 0 or 1;
W, Y and Z are, independently hydrogen, cyano, nitro, halogen, $N_3$, $C_{1-6}$ alkyl, $C_{1-6}$ alkoxy, $C_{1-6}$ haloalkyl, $C_{1-6}$ haloalkoxy, $C_{1-6}$ alkylthio, $C_{3-6}$ cycloalkyl, $CO_2H$, $CO_2(C_{1-6}$ alkyl), $CONR^5R^6$, $COR^{10}$, $SO_2R^{12}$, methylenedioxy, $NHCOR^{11}$ or heterocyclyl;
$R^2$ is aryl or heteroaryl optionally substituted by cyano, nitro, halogen, $N_3$, $C_{1-6}$ alkyl, $C_{1-6}$ alkoxy, $C_{1-6}$ haloalkyl, $C_{1-6}$ haloalkoxy, $C_{1-6}$ alkylthio, $C_{3-6}$ cycloalkyl, $CO_2H$, $CO_2(C_{1-6}$ alkyl), $CONR^3R^{14}$, $COR^{15}$, $SO_2R^{16}$, methylenedioxy, $NHCOR^{17}$ or heterocyclyl;
$R^3$ is $C_{1-4}$ alkyl or $C_{1-4}$ haloalkyl;
$R^4$ is $CO(C_{1-4}$ alkyl) or $CO(C_{1-4}$ haloalkyl);
X is O, S, SO, $SO_2$, $CR^7R^8$ or $NR^9$;
$R^5$, $R^6$, $R^7$, $R^8$, $R^{13}$ and $R^{14}$ are, independently, hydrogen or $C_{1-6}$ alkyl;
$R^9$ is hydrogen, $C_{1-6}$ alkyl or $CO(C_{1-4}$ alkyl);
$R^{10}$, $R^{11}$, $R^{12}$, $R^{15}$, $R^{16}$ and $R^{17}$ are, independently, $C_{1-6}$ alkyl or phenyl;
or a pharmaceutically acceptable salt thereof; or a solvate thereof;

provided that the compound of formula (I) is not a compound of formula (Iz):

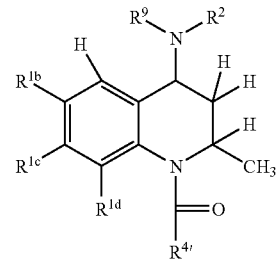

(Iz)

wherein

| $R^{1b}$ | $R^{1d}$ | $R^{1c}$ | $R^{4'}$ | $R^2$ | $R^9$ |
|---|---|---|---|---|---|
| H | H | H | n-butyl | $C_6H_5$ | H |
| H | H | H | n-propyl | $C_6H_5$ | $COCH_3$ |
| H | H | H | n-propyl | $C_6H_5$ | H |
| H | H | H | Ethyl | $C_6H_5$ | H |
| Br | H | H | Methyl | $C_6H_5$ | $COCH_3$ |
| Methyl | H | H | Methyl | 4-$CH_3$—$C_6H_4$ | H |
| Methyl | Methyl | H | Methyl | 2,4-$(CH_3)_2$—$C_6H_3$ | H |
| H | H | H | Methyl | $C_6H_5$ | H |
| $NO_2$ | H | H | Methyl | 4-$NO_2$—$C_6H_4$ | $COCH_3$ |
| $NO_2$ | H | H | Methyl | $C_6H_5$ | $COCH_3$ |
| Cl | H | H | Methyl | $C_6H_5$ | $COCH_3$ |
| H | H | H | Methyl | $C_6H_5$ | $COCH_3$ |
| H | H | H | Methyl | 2,4-$Br_2$—$C_6H_3$ | $COCH_3$ | in free base or unsolvated form.

Alkyl groups are straight or branched chain and are, for example, methyl, ethyl, n-propyl, iso-propyl or n-butyl. Alkoxy is, for example, methoxy, ethoxy, n-propoxy, iso-propoxy, n-butoxy or tert-butoxy.

Cycloalkyl is, for example, cyclopropyl, cyclopentyl or cyclohexyl.

Halogen includes chlorine, fluorine and bromine.

Haloalkyl groups peferably comprise fluorine, chlorine or bromine atoms, and haloalkyl is, for example, $CF_3$, while haloalkoxy is, for example, $OCF_3$.

Aryl is, for example, phenyl or naphthyl.

Heteroaryl is, for example, an aromatic monocyclic 5- or 6-membered ring comprising one, two or three heteroatoms selected from the group comprising nitrogen, oxygen and sulphur. Heteroaryl is, for example, pyridine, pyridazine, pyrimidine, pyrazine, pyrrole, pyrazole, imidazole, 1,2,3-triazole, 1,2,4-triazole, furan, thiophene, oxazole, is isoxazole, thiazole or isothiazole.

Heterocyclyl is a 5- or 6-membered ring comprising one or two nitrogen atoms and, optionally, one oxygen or sulphur atom. Heterocyclyl is, for example, morpholinyl, piperidinyl or pyrrolidinyl. Heterocyclyl may also be thiomorpholinyl. Heterocyclyl is optionally substituted by $C_{1-4}$ alkyl.

Salts of the compounds of formula (I) are preferably pharmaceutically acceptable salts. Pharmaceutically acceptable salts of compounds of the present invention are, for example, acid addition salts (such as hydrochloride, hydrobromide or acetate salts).

Solvates of the compounds or salts of the present invention are conveniently hydrates, such as monohydrates or dihydrates.

Compounds of the present invention include all stereoisomers and mixtures thereof in all proportions.

In one particular aspect the present invention provides a compound of formula (I):

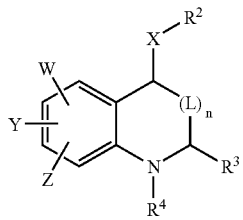

(I)

wherein: L is $CH_2$, O or S; n is 0 or 1; W, Y and Z are, independently, hydrogen, cyano, nitro, halogen, $N_3$, $C_{1-6}$ alkyl, $C_{1-6}$ alkoxy, $C_{1-6}$ haloalkyl, $C_{1-6}$ haloalkoxy, $C_{1-6}$ alkylthio, $C_{3-6}$ cycloalkyl, $CO_2H$, $CO_2(C_{1-6}$ alkyl), $CONR^5R^6$, $COR^{10}$, $SO_2R^{12}$, methylenedioxy, $NHCOR^{11}$ or heterocyclyl; $R^2$ is aryl or heteroaryl optionally substituted by cyano, nitro, halogen, $N_3$, $C_{1-6}$ alkyl, $C_{1-6}$ alkoxy, $C_{1-6}$ haloalkyl, $C_{1-6}$ haloalkoxy, $C_{1-6}$ alkylthio, $C_{3-6}$ cycloalkyl, $CO_2H$, $CO_2(C_{1-6}$ alkyl), $CONR^{13}R^{14}$, $COR^{15}$, $SO_2R^{16}$, methylenedioxy, $NHCOR^{17}$ or heterocyclyl; $R^3$ is $C_{1-4}$ alkyl or $C_{1-4}$ haloalkyl; $R^4$ is $CO(C_{1-4}$ alkyl) or $CO(C_{1-4}$ haloalkyl); X is O, S, SO, $SO_2$, $CR^7R^8$ or $NR^9$; $R^5$, $R^6$, $R^7$, $R^8$, $R^{13}$ and $R^{14}$ are, independently, hydrogen or $C_{1-6}$ alkyl; $R^9$ is hydrogen, $C_{1-6}$ alkyl or $CO(C_{1-4}$ alkyl); $R^{10}$, $R^{11}$, $R^{12}$, $R^{15}$, $R^{16}$ and $R^{17}$ are, independently, $C_{1-6}$ alkyl or phenyl; or a pharmaceutically acceptable salt thereof; or a solvate thereof; provided that the compound of formula (I) is not a compound of formula (Iz):

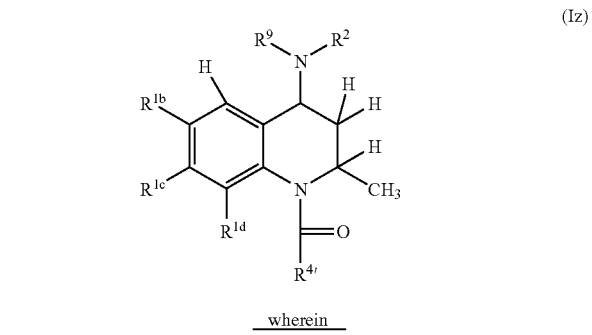

wherein

| $R^{1b}$ | $R^{1d}$ | $R^{1c}$ | $R^{4'}$ | $R^2$ | $R^9$ |
|---|---|---|---|---|---|
| H | H | H | n-butyl | $C_6H_5$ | H |
| H | H | H | n-propyl | $C_6H_5$ | $COCH_3$ |
| H | H | H | n-propyl | $C_6H_5$ | H |

-continued

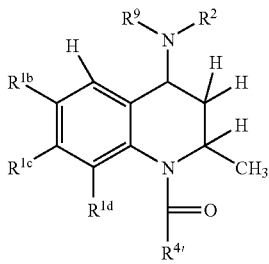

(Iz)

wherein

| $R^{1b}$ | $R^{1d}$ | $R^{1c}$ | $R^{4'}$ | $R^2$ | $R^9$ |
|---|---|---|---|---|---|
| H | H | H | Ethyl | $C_6H_5$ | H |
| Br | H | H | Methyl | $C_6H_5$ | $COCH_3$ |
| Methyl | H | H | Methyl | $4\text{-}CH_3\text{—}C_6H_4$ | H |
| Methyl | Methyl | H | Methyl | $2,4\text{-}(CH_3)_2\text{—}C_6H_3$ | H |
| H | H | H | Methyl | $C_6H_5$ | H |
| $NO_2$ | H | H | Methyl | $4\text{-}NO_2\text{—}C_6H_4$ | $COCH_3$ |
| $NO_2$ | H | H | Methyl | $C_6H_5$ | $COCH_3$ |
| Cl | H | H | Methyl | $C_6H_5$ | $COCH_3$ |
| H | H | H | Methyl | $C_6H_5$ | $COCH_3$ |
| H | H | H | Methyl | $2,4\text{-}Br_2\text{—}C_6H_3$ | $COCH_3$ |
| H | H | Methyl | Methyl | $4\text{-}C_2H_5\text{—}C_6H_4$ | H |
| H | H | H | Methyl | $C_6H_5$ | CO-n-propyl |
| H | H | H | Methyl | $C_6H_5$ | CO-t-butyl |
| H | H | H | $CH_3CH\text{—}CH_3$ | $C_6H_5$ | H |
| H | H | H | $CF_3$ | $C_6H_5$ | $COCF_3$ |
| H | H | H | Ethyl | $C_6H_5$ | $COCH_3$ |
| H | H | H | iso-Pr | $C_6H_5$ | $COCH_3$ |
| H | H | H | iso-Pr | $C_6H_5$ | H |
| H | H | H | Methyl | $C_6H_5$ | CO-n-butyl |
| H | H | H | Methyl | $C_6H_5$ | CO-ethyl |
| H | H | H | n-butyl | $C_6H_5$ | $COCH_3$ |
| H | H | H | Methyl | $C_6H_5$ | CO-i-propyl |
| H | H | H | Ethyl | $C_6H_5$ | CO-ethyl |
| H | H | H | $CH_3CH_2$ | $C_6H_5$ | H | in free base or unsolvated form.

In another aspect of the invention W and Y are both hydrogen. In yet another aspect W, Y and Z are, independently, for example, hydrogen, chloro, cyano, $CO_2(C_{1-4}$ alkyl) (such as $CO_2Me$ or $CO_2Et$) or $C_{1-4}$ alkoxy (such as methoxy).

In a further aspect $R^2$ is, for example, optionally substituted phenyl, such as phenyl optionally substituted by chloro, cyano, $CO_2(C_{1-4}$ alkyl) (such as $CO_2Me$ or $CO_2Et$) or $C_{1-4}$ alkoxy (such as methoxy).

The variable $R^3$ is, for example methyl or ethyl; but is preferably methyl.

The variable $R^4$ is, for example, acetyl.

The variable X is, for example, $NR^9$, wherein $R^9$ is hydrogen or COMe.

It is preferred that L is $CH_2$ and that n is 1.

In a still further aspect the present invention provides a compound of formula (Ia):

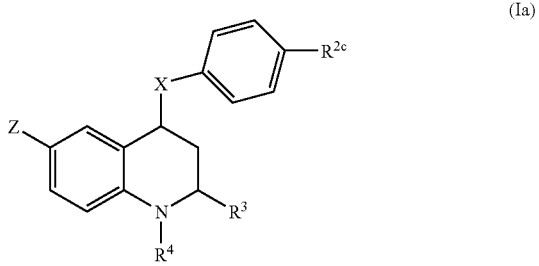

(Ia)

wherein Z, $R^3$, $R^4$ and X are as hereinbefore defined, and $R^{2c}$ is hydrogen, cyano, nitro, is halogen, $N_3$, $C_{1-6}$ alkyl, $C_{1-6}$ alkoxy, $C_{1-6}$ haloalkyl, $C_{1-6}$ haloalkoxy, $C_{1-6}$ alkylthio, $C_{3-6}$ cycloalkyl, $CO_2H$, $CO_2(C_{1-6}$ alkyl), $CONR^{13}R^{14}$, $COR^{15}$, $SO_2R^{16}$, methylenedioxy, $NHCOR^{17}$ or heterocyclyl; wherein $R^{13}$, $R^{14}$, $R^{15}$, $R^{16}$ and $R^{17}$ are as defined above, or a pharmaceutically acceptable salt thereof; or a solvate thereof.

In another aspect the present invention provides a compound of formula (Ia) wherein Z and $R^{2c}$ are independently selected from the group consisting of: hydrogen, $C(O)_2CH_3$, iodo, $N_3$, bromo, methyl, $C(O)_2CH_2CH_3$, cyano and methoxy; provided that Z and $R^{2c}$ are not both hydrogen or methyl.

In yet another aspect the present invention provides a compound of formula (Ia) wherein $R^3$ is methyl; $R^4$ is $C(O)CH_3$; and X is NH; and: Z and $R^{2c}$ are both $CO_2CH_3$; or Z is iodo and $R^{2c}$ is hydrogen; or Z and $R^{2c}$ are both iodo; or Z and $R^{2c}$ are both $N_3$; or Z and $R^{2c}$ are both bromo; Z and $R^{2c}$ are both $CO_2CH_2CH_3$; or Z is hydrogen and $R^{2c}$ is cyano; or Z is methoxy and $R^{2c}$ is $CO_2CH_3$.

In a further aspect the present invention provides a compound of formula (Ib):

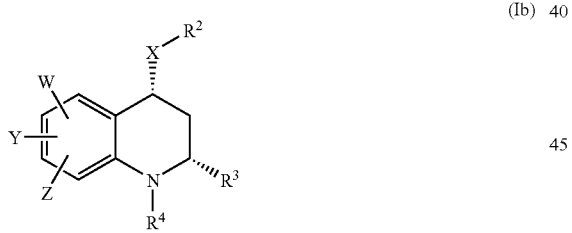

(Ib)

wherein $R^2$, $R^3$, $R^4$, X, Y and Z are as hereinbefore defined, or a pharmaceutically acceptable salt thereof; or a solvate thereof.

In a further aspect the present invention provides a compound of formula (I) wherein the relative configuration of the 2- and 4-position stereocentres is Z with the absolute configuration as depicted in formula (Ib). In a still further aspect the present invention provides a compound of formula (Ib) having an absolute configuration (2S, 4R) and wherein X is NH, $R^3$ is methyl, $R^4$ is $COCH_3$ and W, Y, Z and $R^2$ are as defined above.

In another aspect of the present invention W and Y are both hydrogen and Z is hydrogen, $C(O)_2CH_3$, iodo, $N_3$, bromo, methyl, $C(O)_2CH_2CH_3$, cyano or methoxy.

In a further aspect of the present invention $R^2$ is phenyl para-substituted by $C(O)_2CH_3$, iodo, $N_3$, bromo, methyl, $C(O)_2CH_2CH_3$, cyano or methoxy.

In a further aspect the present invention provides a compound of formula (Ic) wherein the substituent $R^3$ is cis to the substituted amine group at the 4 position of the tetrahydroquinoline:

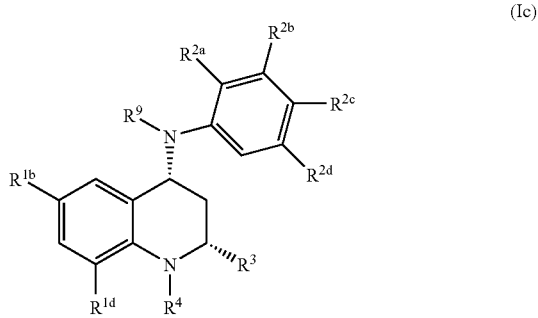

(Ic)

wherein $R^3$, $R^4$ and $R^9$ are as hereinbefore defined;

$R^{1b}$ is H, halogen, $N_3$, $C_{1-6}$ alkyl, $C_{1-6}$ alkoxy, $C_{1-6}$ alkylthio, $C_{3-6}$ cycloalkyl, $CO_2H$, $CO_2(C_{1-6}$ alkyl), $COC_{1-6}$ alkyl, $SO_2Me$ or morpholin-4-yl;

$R^{1d}$ is H or Me;

$R^{2a}$ is H, halogen, $C_{1-6}$ alkyl, $C_{1-6}$ alkoxy or $CONH_2$;

$R^{2b}$ is H, halogen, $C_{1-6}$ alkyl, or methylenedioxy;

$R^{2c}$ is H, cyano, halogen, $N_3$, $C_{1-6}$alkyl, $C_{1-6}$ alkoxy, $C_{1-6}$ alkylthio, $C_{3-6}$ cycloalkyl, $CO_2H$, $CO_2(C_{1-6}$ alkyl), $CONH_2$, $COC_{1-6}$ alkyl, $SO_2Me$, methylenedioxy, NHCOMe or heterocyclyl; and $R^{2d}$ is H, $C_{1-6}$ alkyl, or halogen, or a pharmaceutically acceptable salt thereof; or a solvate thereof.

In a still further aspect the present invention provides a compound of formula (Id):

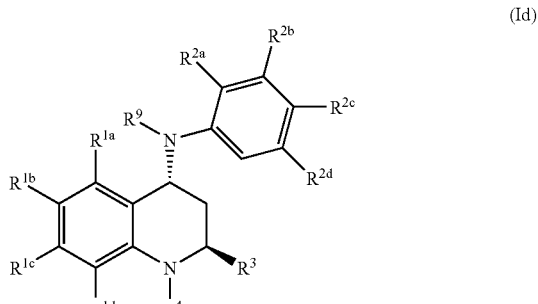

(Id)

wherein wherein $R^{1b}$, $R^{1d}$, $R^{2a}$, $R^{2b}$, $R^{2c}$, $R^{2d}$, $R^3$, $R^4$ and $R^9$ are as hereinbefore defined; $R^{1a}$ is H or $C_{1-6}$ alkyl; and $R^{1c}$ is H or $C_{1-6}$ alkyl; or a pharmaceutically acceptable salt thereof; or a solvate thereof.

In another aspect the present invention provides a compound of formula (Ie):

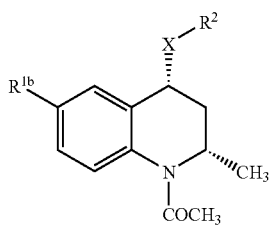

(Ie)

wherein $R^{1b}$ is H, Cl or $CH_3$; X is NH, S, or $CH_2$; and $R^2$ is pyrazin-2-yl or phenyl; or a pharmaceutically acceptable salt thereof; or a solvate thereof.

Compounds of formulae (Ia), (Ib), (Ic), (Id) and (Ie) are sub-groups of compounds of formula (I).

The following Tables provide examples of compounds of the invention. Table I illustrates compounds of formula (Ic); Table II illustrates compounds of formula (Id); and Table III illustrates compounds of formula (Ie).

TABLE I

| Compound | $R^{1b}$ | $R^{1d}$ | $R^{2a}$ | $R^{2b}$ | $R^{2c}$ | $R^{2d}$ | $R^3$ | $R^4$ | $R^9$ |
|---|---|---|---|---|---|---|---|---|---|
| 1 | H | H | H | H | H | H | Me | COMe | H |
| 2 | OMe | H | H | H | OMe | H | Me | COMe | H |
| 3 | Cl | H | H | H | Cl | H | Me | COMe | H |
| 4 | iso-Pr | H | H | H | iso-Pr | H | Me | COMe | H |
| 5 | I | H | H | H | I | H | Me | COMe | H |
| 6 | Br | H | H | H | Br | H | Me | COMe | H |
| 7 | F | H | H | H | F | H | Me | COMe | H |
| 8 | H | H | H | H | H | H | Me | COMe | COMe |
| 9 | Me | H | H | H | Me | H | Me | COMe | H |
| 10 | Et | H | H | H | Et | H | Me | COMe | H |
| 11 | cyclohexyl | H | H | H | cyclohexyl | H | Me | COMe | H |
| 12 | n-Bu | H | H | H | n-Bu | H | Me | COMe | H |
| 13 | SMe | H | H | H | SMe | H | Me | COMe | H |
| 14 | OMe | H | H | H | OMe | H | Me | COMe | COMe |
| 15 | Me | H | H | H | Me | H | Me | COEt | H |
| 16 | $N_3$ | H | H | H | $N_3$ | H | Me | COMe | H |
| 17 | $CO_2H$ | H | H | H | $CO_2H$ | H | Me | COMe | H |
| 18 | $CO_2Me$ | H | H | H | $CO_2Me$ | H | Me | COMe | H |
| 19 | H | H | Cl | H | H | H | Me | COMe | H |
| 20 | H | H | H | Cl | H | H | Me | COMe | H |
| 21 | H | H | H | H | Cl | H | Me | COMe | H |
| 22 | H | H | H | H | Br | H | Me | COMe | H |
| 23 | H | H | H | H | I | H | Me | COMe | H |
| 24 | H | H | OMe | H | H | H | Me | COMe | H |
| 25 | H | H | H | H | OMe | H | Me | COMe | H |
| 26 | H | H | H | Me | H | H | Me | COMe | H |
| 27 | H | H | H | H | Me | H | Me | COMe | H |
| 28 | H | H | Cl | H | Me | H | Me | COMe | H |
| 29 | H | H | Me | H | Cl | H | Me | COMe | H |
| 30 | H | H | Cl | Cl | H | H | Me | COMe | H |
| 31 | H | H | Cl | H | Cl | H | Me | COMe | H |
| 32 | H | H | Cl | H | H | Cl | Me | COMe | H |
| 33 | H | H | H | Cl | Cl | H | Me | COMe | H |
| 34 | H | H | H | Cl | H | Cl | Me | COMe | H |
| 35 | H | H | H | H | cyclohexyl | H | Me | COMe | H |
| 36 | H | H | H | H | CN | H | Me | COMe | H |
| 37 | H | H | H | Methylenedioxy | | H | Me | COMe | H |
| 38 | Cl | H | H | H | Me | H | Me | COMe | H |
| 39 | Cl | H | H | H | Morpholin-4-yl | H | Me | COMe | H |
| 40 | Me | H | H | H | OMe | H | Me | COMe | H |
| 41 | Cl | H | H | H | OMe | H | Me | COMe | H |
| 42 | $CO_2Et$ | H | H | H | $CO_2Et$ | H | Me | COMe | H |
| 43 | H | H | H | H | CN | H | Et | COMe | H |
| 44 | $CO_2CHMe_2$ | H | H | H | $CO_2CHMe_2$ | H | Me | COMe | H |
| 45 | OMe | H | H | H | Cl | H | Me | COMe | H |
| 46 | OMe | H | H | H | Me | H | Me | COMe | H |
| 47 | OMe | H | H | H | Benzoyl | H | Me | COMe | H |
| 48 | Cl | H | H | H | $CO_2Me$ | H | Me | COMe | H |
| 49 | OMe | H | H | H | COMe | H | Me | COMe | H |
| 50 | OMe | H | H | H | $CONH_2$ | H | Me | COMe | H |
| 51 | OMe | H | H | H | CN | H | Me | COMe | H |
| 52 | OMe | H | H | H | $CO_2Me$ | H | Me | COMe | H |
| 53 | H | Me | H | H | CN | H | Me | COMe | H |
| 54 | OMe | H | H | H | Morpholin-4-yl | H | Me | COMe | H |
| 55 | Cl | H | $CONH_2$ | H | H | H | Me | COMe | H |
| 56 | H | H | H | H | $CONH_2$ | H | Me | COMe | H |
| 57 | Me | H | H | H | CN | H | Me | COMe | H |
| 58 | Me | H | H | H | Morpholin-4-yl | H | Me | COMe | H |
| 59 | H | H | $CONH_2$ | H | H | H | Me | COMe | H |
| 60 | H | H | H | H | NHCOMe | H | Me | COMe | H |

TABLE I-continued

| Compound | $R^{1b}$ | $R^{1d}$ | $R^{2a}$ | $R^{2b}$ | $R^{2c}$ | $R^{2d}$ | $R^3$ | $R^4$ | $R^9$ |
|---|---|---|---|---|---|---|---|---|---|
| 61 | Cl | H | H | H | NHCOMe | H | Me | COMe | H |
| 62 | H | H | H | H | $CO_2Me$ | H | Me | COMe | H |
| 63 | OMe | H | H | H | NHCOMe | H | Me | COMe | H |
| 64 | OMe | H | H | H | $SO_2Me$ | H | Me | COMe | H |
| 65 | Br | H | H | H | Benzoyl | H | Me | COMe | H |
| 66 | Morpholin-4-yl | H | H | H | OMe | H | Me | COMe | H |
| 67 | Morpholin-4-yl | H | H | H | CN | H | Me | COMe | H |
| 68 | Morpholin-4-yl | H | H | H | H | H | Me | COMe | H |
| 69 | H | H | H | H | $CO_2Me$ | H | Et | COMe | H |
| 70 | H | H | H | H | H | H | Phenyl | COMe | H |
| 71 | H | H | H | H | CN | H | Me | COMe | H |
| 72 | SMe | H | H | H | H | H | Me | COMe | H |
| 73 | $SO_2Me$ | H | H | H | H | H | Me | COMe | H |
| 74 | I | H | H | H | H | H | Me | COMe | H |
| 75 | Br | H | H | H | H | H | Me | COMe | H |

TABLE II

| Compound | $R^{1a}$ | $R^{1b}$ | $R^{1c}$ | $R^{1d}$ | $R^{2a}$ | $R^{2b}$ | $R^{2c}$ | $R^{2d}$ | $R^3$ | $R^4$ | $R^9$ |
|---|---|---|---|---|---|---|---|---|---|---|---|---|
| 1 | H | H | H | H | H | H | H | H | Me | COMe | H |
| 2 | H | OMe | H | H | H | H | OMe | H | Me | COMe | COMe |
| 3 | H | H | H | H | H | H | H | H | Me | COMe | COMe |
| 4 | H | Cl | H | H | H | H | Cl | H | Me | COMe | COMe |
| 5 | Me | H | Me | H | Me | H | Me | Me | Me | COMe | COMe |
| 6 | H | iso-Pr | H | H | H | H | iso-Pr | H | Me | COMe | COMe |
| 7 | H | I | H | H | H | H | I | H | Me | COMe | COMe |
| 8 | H | F | H | H | H | H | F | H | Me | COMe | COMe |
| 9 | H | Br | H | H | H | H | Br | H | Me | COMe | COMe |
| 10 | H | Me | H | H | H | H | Me | H | Me | COMe | COMe |
| 11 | H | Et | H | H | H | H | Et | H | Me | COMe | COMe |
| 12 | H | Cyclohexyl | H | H | H | H | Cyclohexyl | H | Me | COMe | COMe |
| 13 | H | n-Bu | H | H | H | H | n-Bu | H | Me | COMe | COMe |
| 14 | H | SMe | H | H | H | H | SMe | H | Me | COMe | COMe |
| 15 | H | Me | H | H | H | H | Me | H | Me | COPh | H |
| 16 | H | Me | H | H | H | H | Me | H | Me | COEt | H |
| 17 | H | $N_3$ | H | H | H | H | $N_3$ | H | Me | COMe | COMe |
| 18 | H | $CO_2Me$ | H | H | H | H | $CO_2Me$ | H | Me | COMe | H |
| 19 | H | COMe | H | H | H | H | COMe | H | Me | COMe | COMe |
| 20 | H | $N_3$ | H | H | H | H | $N_3$ | H | Me | COMe | H |
| 21 | H | H | H | H | Cl | H | H | H | Me | COMe | H |
| 22 | H | H | H | H | H | Cl | H | H | Me | COMe | H |
| 23 | H | H | H | H | H | H | Cl | H | Me | COMe | H |
| 24 | H | H | H | H | H | H | Br | H | Me | COMe | H |
| 25 | H | H | H | H | H | H | I | H | Me | COMe | H |
| 26 | H | H | H | H | OMe | H | H | H | Me | COMe | H |
| 27 | H | H | H | H | H | H | OMe | H | Me | COMe | H |
| 28 | H | H | H | H | H | Me | H | H | Me | COMe | H |
| 29 | H | H | H | H | H | H | Me | H | Me | COMe | H |
| 30 | H | H | H | H | Cl | H | Me | H | Me | COMe | H |
| 31 | H | H | H | H | Me | H | Cl | H | Me | COMe | H |
| 32 | H | H | H | H | Cl | Cl | H | H | Me | COMe | H |
| 33 | H | H | H | H | Cl | H | Cl | H | Me | COMe | H |
| 34 | H | H | H | H | Cl | H | H | Cl | Me | COMe | H |
| 35 | H | H | H | H | Cl | Cl | H | H | Me | COMe | H |
| 36 | H | H | H | H | Cl | H | H | Cl | Me | COMe | H |
| 37 | H | H | H | H | H | H | Cyclohexyl | H | Me | COMe | H |
| 38 | H | H | H | H | H | H | CN | H | Me | COMe | H |
| 39 | H | H | H | H | H | Methylenedioxy | | H | Me | COMe | H |
| 40 | H | Cl | H | H | H | Me | H | H | Me | COMe | H |
| 41 | H | Cl | H | H | H | H | Morpholin-4-yl | H | Me | COMe | H |
| 42 | H | Me | H | H | H | H | OMe | H | Me | COMe | H |
| 43 | H | Cl | H | H | H | H | OMe | H | Me | COMe | H |
| 44 | H | H | H | H | H | H | $CO_2Me$ | H | Et | COMe | H |
| 45 | H | H | H | H | H | H | CN | H | Et | COMe | H |
| 46 | H | $CO_2CHMe_2$ | H | H | H | H | $CO_2CHMe_2$ | H | Me | COMe | H |
| 47 | H | OMe | H | H | H | H | Benzoyl | H | Me | COMe | H |
| 48 | H | Cl | H | H | H | H | $CO_2Me$ | H | Me | COMe | H |
| 49 | H | OMe | H | H | H | H | $CONH_2$ | H | Me | COMe | H |
| 50 | H | OMe | H | H | H | H | CN | H | Me | COMe | H |
| 51 | H | OMe | H | H | H | H | $CO_2Me$ | H | Me | COMe | H |
| 52 | H | H | H | Me | H | H | CN | H | Me | COMe | H |
| 53 | H | OMe | H | H | H | H | Morpholin-4-yl | H | Me | COMe | H |
| 54 | H | Cl | H | H | $CONH_2$ | H | H | H | Me | COMe | H |

TABLE II-continued

| Compound | $R^{1a}$ | $R^{1b}$ | $R^{1c}$ | $R^{1d}$ | $R^{2a}$ | $R^{2b}$ | $R^{2c}$ | $R^{2d}$ | $R^3$ | $R^4$ | $R^9$ |
|---|---|---|---|---|---|---|---|---|---|---|---|
| 55 | H | Cl | H | H | H | H | $CONH_2$ | H | Me | COMe | H |
| 56 | H | H | H | H | H | H | $CONH_2$ | H | Me | COMe | H |
| 57 | H | Me | H | H | H | H | CN | H | Me | COMe | H |
| 58 | H | Me | H | H | H | H | Morpholin-4-yl | H | Me | COMe | H |
| 59 | H | H | H | H | $CONH_2$ | H | H | H | Me | COMe | H |
| 60 | H | H | H | H | H | H | NHCOMe | H | Me | COMe | H |
| 61 | H | H | H | H | H | H | $CO_2Me$ | H | Me | COMe | H |
| 62 | H | OMe | H | H | H | H | NHCOMe | H | Me | COMe | H |
| 63 | H | Morpholin-4-yl | H | H | H | H | CN | H | Me | COMe | H |
| 64 | H | Morpholin-4-yl | H | H | H | H | H | H | Me | COMe | H |
| 65 | H | SMe | H | H | H | H | H | H | Me | COMe | H |

TABLE III

| Compound No. | $R^{1b}$ | X | $R^2$ |
|---|---|---|---|
| 1 | H | NH | Pyrazin-2-yl |
| 2 | Cl | NH | Pyrazin-2-yl |
| 3 | H | NH | Pyridin-4-yl |
| 4 | $CH_3$ | S | Phenyl |
| 5 | H | $CH_2$ | Phenyl |

According to the invention there is further provided a process for the preparation of a compound of formula (I) which comprises reacting a compound of formula (II):

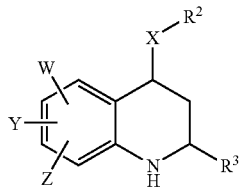
(II)

with a suitable acid anhydride in the presence of a suitable base (such as pyridine) at a suitable temperature (such as room temperature). A compound of formula (II), wherein W and Y are both hydrogen, Z is at the 6-position, $R^2$ is para-substituted phenyl where its substituent is the same as Z, and $R^3$ is methyl, can be prepared by a Doebner-von Miller type reaction, that is by reacting an aniline of formula (III):

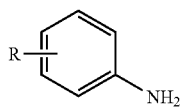
(III)

wherein R is Z or the substituent on $R^2$, with acetaldehyde in a suitable solvent (for example ethanol/water) at a suitable temperature (such as room temperature).

Alternatively, a compound of formula (I) can be prepared by reacting a compound of formula (IV):

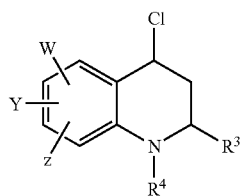
(IV)

with a compound of formula (V):

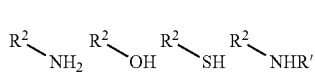
(V)

wherein R' is alkyl, in a suitable solvent (such as acetonitrile) with a suitable base and at a suitable temperature (such as reflux). A compound of formula (IV) can be prepared by chlorinating a compound of formula (VI):

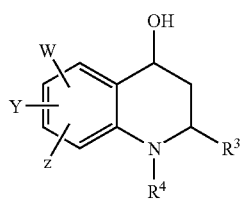
(VI)

with a suitable chlorinating reagent (such as thionyl chloride) in a suitable solvent (such as dichloromethane). A compound of formula (VI) can be prepared by acylating a compound of formula (VII):

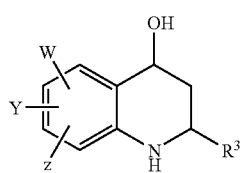
(VII)

(for example with an acid anhydride $(R^4)_2O$) in a suitable solvent (such as dichloromethane). A compound of formula (VII) can be prepared by reacting an aniline of formula (VIII):

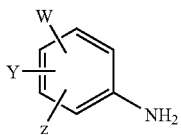
(VIII)

with a compound of formula (IX):

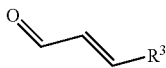
(IX)

in the presence of a suitable acid and solvent (such as aqueous 5% hydrochloric acid).

Alternatively, a compound of formula (VI) can be prepared by acetylation (for example with an acid anhydride $(R^4)_2O$) and subsequent reduction of a compound of is formula (X):

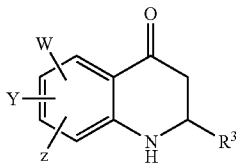
(X)

Alternatively compounds of formula (I) can be prepared as shown in Scheme 1 below. Both racemic and enantioselective synthesis can be prepared by this route.

Compounds of formula (Ib) can be prepared as shown in Scheme 2 below.

Compounds of formulae (III) and (IX) are commercially available or can be prepared using or adapting literature methods.

In another aspect the present invention provides processes for the preparation of a compound of formula (I), (Ia), (Ib), (Ic), (Id) or (Ie).

Compounds of the invention are useful because they demonstrate pharmacological activity. In particular they demonstrate activity as modulators of the STAT6 signal pathway. The compounds of the invention, being modulators of the STAT6 pathway, can be used to treat atopic dermatitis, urticaria, allergic asthma, allergic rhinitis, food allergies, allergic conjunctivitis, hayfever, bullous pemphigoid, industrial sensitisation or chronic rejection of transplants, or COPD.

The present invention also provides a compound of formula (I):

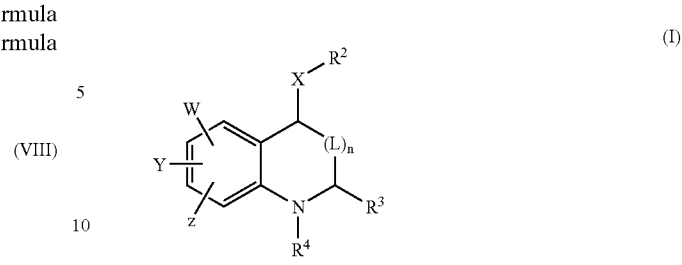
(I)

wherein:
L is $CH_2$, O or S;
n is 0 or 1;
W, Y and Z are, independently hydrogen, cyano, nitro, halogen, $N_3$, $C_{1-6}$ alkyl, $C_{1-6}$ alkoxy, $C_{1-6}$ haloalkyl, $C_{1-6}$ haloalkoxy, $C_{1-6}$ alkylthio, $C_{3-6}$ cycloalkyl, $CO_2H$, $CO_2(C_{1-6}$ alkyl), $CONR^5R^6$, $COR^{10}$, $SO_2R^{12}$, methylenedioxy, $NHCOR^{11}$ or heterocyclyl;
$R^2$ is aryl or heteroaryl optionally substituted by cyano, nitro, halogen, $N_3$, $C_{1-6}$ alkyl, $C_{1-6}$ alkoxy, $C_{1-6}$ haloalkyl, $C_{1-6}$ haloalkoxy, $C_{1-6}$ alkylthio, $C_{3-6}$ cycloalkyl, $CO_2H$, $CO_2(C_{1-6}$ alkyl), $CONR^{13}R^{14}$, $COR^{15}$, $SO_2R^{16}$, methylenedioxy, $NHCOR^{17}$ or heterocyclyl;
$R^3$ is $C_{1-4}$ alkyl or $C_{1-4}$ haloalkyl;
$R^4$ is $CO(C_{1-4}$ alkyl) or $CO(C_{1-4}$ haloalkyl);
X is O, S, SO, $SO_2$, $CR^7R^8$ or $NR^9$;
$R^5$, $R^6$, $R^7$, $R^8$, $R^{13}$ and $R^{14}$ are, independently, hydrogen or $C_{1-6}$ alkyl;
$R^9$ is hydrogen, $C_{1-6}$ alkyl or $CO(C_{1-4}$ alkyl);
$R^{10}$, $R^{11}$, $R^{12}$, $R^{15}$, $R^{16}$ and $R^{17}$ are, independently, $C_{1-6}$ alkyl or phenyl;
or a pharmaceutically acceptable salt thereof; or a solvate thereof, for use in medical therapy. The term 'medical therapy' as used herein is intended to include prophylactic, diagnostic and therapeutic regimens carried out in vivo or ex vivo on humans or other mammals.

According to the invention there is further provided the use of a compound of invention of formula (I) as defined anywhere above, (Ia), (Ib), (Ic), (Id) or (Ie), or a pharmaceutically acceptable salt thereof; or solvate thereof, in the manufacture of a medicament for use in therapy (such as in the modulation of the STAT6 signal pathway; for example in the treatment of atopic dermatitis, urticaria, allergic asthma, allergic rhinitis, a food allergy, allergic conjunctivitis, hayfever, bullous pemphigoid, industrial sensitization, chronic rejection of transplants or COPD; especially allergic asthma, or allergic rhinitis, or COPD) in a mammal (such as a human).

A method of treating STAT6 mediated disease state {such as atopic dermatitis, urticaria, allergic asthma, allergic rhinitis, a food allergy, allergic conjunctivitis, hayfever, bullous pemphigoid, industrial sensitization, chronic rejection of transplants or COPD; especially allergic asthma, or allergic rhinitis, or COPD} in a mammal (such as a human) which comprises administering to a mammal in need of such treatment an effective amount of a compound of formula (I), (Ia), (Ib), (Ic), (Id) or (Ie), or a pharmaceutically acceptable salt thereof; or a solvate thereof.

The dose of the compound to be administered will depend on the relevant indication, the age, weight and sex of the patient and may be determined by a physician. The dosage will preferably be in the range of from 0.01 mg/kg to 10 mg/kg.

The compounds may be administered topically, e.g. to the lung and/or the airways, in the form of solutions, suspensions, HFA aerosols or dry powder formulations, for example formulations in the inhaler device known as the TURBUHALER®; or systemically, for example by oral administration in the form of a tablet, pill, capsule, syrup, powder or granule, or by parenteral administration, for example, in the form of sterile parenteral solution or suspension, or by rectal administration, for example in the form of suppositories.

The compounds of the invention may be administered on their own or as a pharmaceutical comprising the compound of the invention in combination with a pharmaceutically acceptable diluent, adjuvant and/or carrier. Particularly preferred are compositions not containing material capable of causing an adverse, such as an allergic, reaction. Also provided by the present invention is a pharmaceutical composition comprising a compound according to the present invention, as active ingredient, together with a pharmaceutically acceptable adjuvant, diluent or carrier.

Dry powder formulations and pressurized HFA aerosols of the compounds of the invention may be administered by oral or nasal inhalation. For inhalation the compound is desirably finely divided. The finely divided compound preferably has a mass median diameter of less than 10 μm, and may be suspended in a propellant mixture with the assistance of a dispersant, such as a $C_8$–$C_{20}$ fatty acid or salt thereof, (such as oleic acid), a bile salt, a phospholipid, an alkyl saccharide, a perfluorinated or polyethoxylated surfactant, or other pharmaceutically acceptable dispersant.

The compounds of the invention may also be administered by means of a dry powder inhaler. The inhaler may be a single or a multi dose inhaler, and may be a breath actuated dry powder inhaler.

One possibility is to mix the finely divided compound with a carrier substance, for example a mono-, di- or polysaccharide, a sugar alcohol, or another polyol. Suitable carriers are sugars, for example lactose, glucose, raffinose, melezitose, lactitol, maltitol, trehalose, sucrose or mannitol; and starch. Alternatively the finely divided compound may be coated by another substance. The powder mixture may also be dispensed into hard gelatin capsules, each containing the desired dose of the active compound.

Another possibility is to process the finely divided powder into spheres which break up during the inhalation procedure. This spheronized powder may be filled into the drug reservoir of a multidose inhaler, for example that known as the TURBUHALER® in which a dosing unit meters the desired dose which is then inhaled by the patient. With this system the active compound, with or without a carrier substance, is delivered to the patient.

For oral administration the active compound may be admixed with an adjuvant or a carrier, for example lactose, saccharose, sorbitol or mannitol; a starch, for example potato starch, corn starch or amylopectin; a cellulose derivative; a binder, for example gelatin or polyvinylpyrrolidone, and/or a lubricant, for example magnesium stearate, calcium stearate, polyethylene glycol, a wax, paraffin, or the like, and then compressed into tablets. If coated tablets are required, the cores, prepared as described above, may be coated with a concentrated sugar solution which may contain for example gum arabic, gelatin, talcum, titanium dioxide, and the like. Alternatively, the tablet may be coated with a suitable polymer dissolved in a readily volatile organic solvent.

For the preparation of soft gelatin capsules, the compound may be admixed with for example a vegetable oil or polyethylene glycol. Hard gelatin capsules may contain granules of the compound using either the above mentioned excipients for tablets. Also liquid or semisolid formulations of the drug may be filled into hard gelatin capsules.

Liquid preparations for oral application may be in the form of syrups or suspensions, for example solutions containing the compound, the balance being sugar and a mixture of ethanol, water, glycerol and propylene glycol. Optionally such liquid preparations may contain coloring agents, flavoring agents, saccharine and/or carboxymethylcellulose as a thickening agent or other excipients known to those skilled in art.

The compounds of the invention may be administered in conjunction with other compounds used for the treatment of the above conditions.

The following Examples illustrate the invention. Throughout the Examples all reactions were performed in dried glassware in an argon or nitrogen atmosphere at room temperature, unless otherwise noted. All solvents and reagents were used as received.

$^1$H-NMR spectra were recorded at 400 MHz. The residual solvent peak, usually chloroform ($\delta_H$ 7.27 ppm) was used as internal shift reference. Analytical HPLC was run on a Hewlett Packard LC-MS 1100, using a C-18 reversed phase column and eluting with the following general system: acetonitrile:0.1M NH$_4$OAc (20:80 to 90:10 gradient)

Preparative LC was run on a Kromasil KR-100-10-C18 column (250×20 mm), using different proportions of acetonitrile:water containing 2.0% HOAc or acetonitrile:0.1M NH$_4$OAc, as eluent. Chiral separations was performed on Chiralpak AD columns using different proportions of hexane, 2-propanol, methanol and diethylamine. Flash chromatography was performed on silica (Merck 40–63 μm) with the eluents indicated in the specific Examples.

EXAMPLE 1

This Example illustrates the preparation of cis-1-Acetyl-6-ethyl-N-(4-ethylphenyl)-1,2,3,4-tetrahydro-2-methyl-4-quinolinamine (Compound No. 10 Table I)

Step 1: cis-6-Ethyl-N-(4-ethylphenyl)-2-methyl-1,2,3,4-tetrahydro-4-quinolinamine Acetaldehyde (0.77 g, 17.4 mmol) was added to an ice-cooled solution of p-ethylaniline (0.71 g, 5.8 mmol) in aqueous ethanol (20 ml, 60%). After stirring at room temperature for 24 hours the solvents were evaporated. The crude product was purified on silica (ethyl acetate:heptane 1:4) and preparative HPLC to yield the cis:trans isomers in a 1:2 ratio to provide the sub-titled product (0.65 mmol). (The corresponding trans-isomer was also isolated 1.3 mmol.)

Step 2: cis-1-Acetyl-6-ethyl-N-(4-ethylphenyl)- 1,2,3,4-tetrahydro-2-methyl-4-quinolinamine.

The compound of Step 1 (59 mg, 0.20 mmol) was dissolved in pyridine (1 ml) and acetic anhydride (2.0 mmol) was added. After stirring at room temperature for 20 hours the solvent was evaporated and the crude product was purified on silica (ethyl acetate:heptane 1:2). The title compound was obtained as a colorless oil (0.12 mmol).

$^1$H NMR CDCl$_3$: δ 7.23 (1H, s); 7.16–7.00 (4H, m); 6.63 (2H, d); 4.90 (1H, br s); 4.24–4.14 (1H, m); 3.82–3.68 (1H, m); 2.70–2.52 (5H, m); 2.20 (3H, s); 1.38–1.15 (10H, m).

EXAMPLE 2

This Example illustrates the preparation of 4-{[(2S*,4R*)-1-acetyl-2-methyl-1,2,3,4-tetrahydro-4-quinolinyl]amino}benzonitrile (Compound No. 36 of Table I) and the preparation of 4-[{(2R*,4R*)1-acetyl-1,2,3,4-tetrahydro-2-methyl-4-quinolinyl}amino]-benzonitrile. (Compound No. 45 Table II).

Step 1: 1-(4-Hydroxy-2-methyl-3,4-dihydro-2H-quinolin-1-yl)-ethanone.

A solution of 1,2,3,4-tetrahydro-2-methyl-4-quinolinol (5.9 g, 36.4 mmol) and acetic anhydride (37.1 g, 364 mmol) in dichloromethane (100 ml) was stirred for one hour. The solvents were evaporated and the crude product was purified on silica (ethyl acetate:heptane 1:1) to obtain the sub-titled product (33.5 mmol).

Step 2:

1-(4-Hydroxy-2-methyl-3,4-dihydro-2H-quinolin-1-yl)-ethanone (3.1 g, 15 mmol) was dissolved in dry dichloromethane (50 ml). Thionyl chloride (1.96 g, 16.5 mmol) was added at −10° C. and the reaction mixture was stirred vigorously for about 30 minutes. The reaction mixture was filtered through a short plug of silica and eluted with dichloromethane. The solvents were removed by reduced pressure affording a yellowish oil (2.15 g).

The oil was dissolved in dry acetonitrile (60 ml) and 4-aminobensonitrile (3.54 g, 30 mmol) was added. The flask was sealed and heated at 80° C. for 12 h. The solvent was removed at reduced pressure and the crude product was purified on silica using ethyl acetate:heptane 1:1 as eluent, affording the product (4.6 mmol). The product was further purified on preparative HPLC to yield the cis/trans diastereomers in a 2:3 ratio (1.8 mmol of the cis compound and 2.7 mmol of the trans compound) as white solids after lyophilisation. The enantiomers were resolved according to the general procedures.

Compound No. 36 of Table I: $[\alpha]_D^{20}$=171° (c=0.28, $CH_2Cl_2$); $^1$H NMR $CDCl_3$: δ 7.46 (2H, d); 7.32 (1H, dt); 7.24–7.14 (3H, m); 6.63 (2H, d); 5.00–4.88 (1H, m); 4.42 (1H, br d); 4.31–4.23 (1H, m); 2.73–2.63 (1H, m); 2.20 (3H, s); 1.34 (1H, q); 1.17 (3H, d).

Compound No. 45 Table II: $[\alpha]_D^{20}$=56° (c=0.53, $CH_2Cl_2$); $^1$H NMR $CDCl_3$: δ 7.45–7.18 (6H, m); 6.62 (2H, d); 5.0–4.85 (1H, m); 4.62 (1H, t); 4.40 (1H, d); 2.58–2.49 (1H, m); 2.18 (3H, s); 1.82–1.75 (1H, m); 1.20 (3H, d).

EXAMPLE 3

This Example illustrates the preparation of (2S,4R)-1-Acetyl-2-methyl-N-phenyl-1,2,3,4-tetrahydro-4-quinolinamine (Compound No. 1 of Table I).

Step 1: 1-[(2S)-2-methyl-4-(phenylimino)-3,4-dihydro-1(2H)-quinolinyl]-1-ethanone.

A solution of (2S)-1-acetyl-2-methyl-2,3-dihydro-4(1H)-quinolinone (20 mg, 0.098 mmol; preparation see Tetrahedron: Asymmetry (1998), 9(7), 1137–1142), aniline (36 μl, 0.394 mmol) and a catalytic amount of p-toluene sulfonic acid monohydrate was refluxed overnight in toluene (4 ml) containing molcular sieve 3 Å (0.9 g). The resulting mixture was filtered, concentrated and purified on silica (ethyl acetate:heptane 1:2) to obtain the sub-titled product (22.8 mg, 0.082 mmol).

Step 2: (2S, 4R)-1-Acetyl-2-methyl-N-phenyl-1,2,3,4-tetrahydro-4-quinolinamine.

A solution of the product of Step 2 (13 mg, 0.047 mmol) in ethyl acetate (5 ml) was hydrogenated for four hours at 1 atmosphere in the presence of palladium on charcoal (15 mg, 10%). The mixture was filtered and the residue was concentrated and purified on silica (ethyl acetate:heptane 1:2). The title compound was obtained as a colorless oil (0.025 mmol). $[\alpha]_D^{20}$=236° (c0.53, $CH_2Cl_2$).

$^1$H NMR $CDCl_3$: δ 7.37–7.11 (6H, m); 6.77 (1H, t); 6.66 (2H, d); 4.92 (1H, br d); 4.22 (1H, dd); 4.14–3.60 (1H, br s); 2.70–2.61 (1H, m); 2.18 (3H, s); 1.35–1.22 (1H, m); 1.17 (3H, d).

EXAMPLE 4

This Example illustrates the preparation of cis-1-acetyl-2,6-dimethyl-1,2,3,4-tetrahydro-4-quinolinyl phenyl sulfide (Compound No. 4 of Table III).

To a mixture of 1-acetyl-4-chloro-1,2,3,4-tetrahydro-2,6-dimethyl-quinoline (200 mg, 0.84 mmol) and sodium hydride (20 mg) in THF (2 ml) was added a solution of benzenethiol (66 μl, 1.2 mmol) in THF (1 ml). The mixture was stirred for 16 hrs. Water was added and the product was extracted with ethyl acetate. The crude product was purified on silica (ethyl acetate/heptane) and with preparative HPLC to yield the sub-title product (0.18 mmol) together with its trans isomer (0.12 mmol).

$^1$H NMR $CDCl_3$: δ 7.42–7.40 (6H, m); 7.21 (1H, d); 7.04–6.95 (1H, d); 4.81 (1H, s); 4.03 (1H, dd); 2.62 (1H, m); 2.39 (3H, s); 2.16 (3H, s); 1.41–1.32 (1H, m); 1.12 (3H, d).

EXAMPLE 5

This Example illustrates the preparation of cis-1-Acetyl-2-methyl-4-(phenylmethyl)-1,2,3,4-tetrahydroquinoline (Compound No. 5 of Table III).

To a solution of (2S)-1-acetyl-2-methyl-2,3-dihydro-4 (1H)-quinolinone (100 mg, 0.49 mmol) in dry toluene (5 ml) was added benzyl magnesium chloride (0.98 mmol, 1.3M in THF). The solution was refluxed for 5 hrs and then quenched with aqueous sulfuric acid. The aqueous phase was extracted with ether, the solvents were evaporated and the crude product was purified on silica (ethyl acetate/heptane) to obtain a yellow oil (79 mg). The oil was dissolved in THF (3 ml) and aqueous sulfuric (2M, 10 ml) acid was added. The solution was stirred over night, extracted with ether and the solvents were evaporated to a yellow oil (40 mg). The crude product was dissolved in ethyl acetate (10 mg) and was hydrogenated for 16 hours at 1 atmosphere in the presence of palladium on charcoal (100 mg, 10%). The mixture was filtered and the residue was concentrated and purified with preparative HPLC. The title compound was obtained as colorless oil (16 mg, 0.20 mmol).

$^1$H NMR $CDCl_3$: δ 7.39–7.21 (8H, m); 7.17 (1H, br d); 4.87 (1H, br s); 3.48 (1H, dd); 2.79–2.65 (1H, m); 3.62 (1H, dd); 2.29–2.22 (1H, m); 2.17 (3H, s); 1.02 (3H, d); 0.90–0.81 (1H, m).

Proton NMR data are provided for compounds of formula (I).

cis-1-Acetyl-1,2,3,4-tetrahydro-6-methoxy-N-(4-methoxyphenyl)-2-methyl-4-quinolinamine (Compound No. 2 Table I).

$^1$H NMR $CDCl_3$: δ 7.03 (1H, br d); 6.92 (1H, d); 6.78 (3H, m); 6.61 (2H, d); 4.90 (1H, br s); 4.09 (1H, br d); 3.76 (3H, s); 3.73 (3H, s); 3.50 (1H, br s); 2.66–2.57 (1H, m); 2.14 (3H, s); 1.22–1.05 (4H, m).

cis-1-Acetyl-6-chloro-N-(4-chlorophenyl)-1,2,3,4-tetrahydro-2-methyl-4-quinolinamine (Compound No. 3 Table I).

$^1$H NMR CDCl$_3$: δ 7.29–7.21 (1H, m); 7.19–7.03 (4H, m); 6.54 (2H, d); 4.86 (1H, br s); 4.14–4.06 (1H, m); 3.85 (1H, d); 2.67–2.59 (1H, m); 2.17 (3H, s); 1.32–1.19 (1H, m); 1.14 (3H, d).

cis-1-Acetyl-1,2,3,4-tetrahydro-2-methyl-6-(1-methylethyl)-N-[4-(1-methylethyl)phenyl]-4-quinolinamine (Compound No. 4 Table I).

$^1$H NMR CDCl$_3$: δ 7.24 (1H, br s); 7.16–7.03 (4H, m); 6.64 (2H, d); 4.88 (1H, br d); 4.20 (1H, br d); 3.68 (1H, br s); 2.96–2.78 (2H, m); 2.70–2.60 (1H, m); 2.19 (3H, s); 1.33–1.18 (13H, m); 1.16 (3H, d).

cis-1-Acetyl-1,2,3,4-tetrahydro-6-iodo-N-(4-iodophenyl)-2-methyl-4-quinolinamine (Compound No. 5 Table I).

$^1$H NMR CDCl$_3$: δ 7.64 (1H, dd); 7.58 (1H, s); 7.46 (2H, d); 6.91 (1H, br d); 6.42 (2H, d); 4.86 (1H, br d); 4.16–4.07 (1H, m); 3.80 (1H, d); 2.68–2.58 (1H, m); 2.18 (3H, s); 1.35–1.20 (1H, m); 1.16(3H, d).

(2S*,4R*)-1-Acetyl-6-bromo-N-(4-bromophenyl)-1,2,3,4-tetrahydro-2-methyl-4-quinolinamine (Compound No. 6 Table I). $[α]_D^{20}$=267° (c=0.004, CH$_2$Cl$_2$).

$^1$H NMR CDCl$_3$: δ 7.44–7.36 (2H, m); 7.27 (2H, d); 7.02 (1H, br d); 6.49 (2H, d); 4.85 (1H, br s); 4.15–4.05 (1H, m); 3.87 (1H, d); 2.67–2.58 (1H, m); 2.17 (3H, s); 1.34–1.18 (1H, m); 1.14(3H, d).

cis-1-Acetyl-6-fluoro-N-(4-fluorophenyl)-1,2,3,4-tetrahydro-2-methyl-4-quinolinamine (Compound No. 7 Table I).

$^1$H NMR CDCl$_3$: δ 7.16–6.86 (5H, m); 6.60–6.53 (2H, m); 4.91 (1H, br s); 4.14–4.04 (1H, m), 3.75 (1H, d); 2.70–2.60 (1H, m); 2.17 (3H, s); 1.34–1.18 (1H, m); 1.14 (3H, d).

(2S*,4R*)-1-Acetyl-1,2,3,4-tetrahydro-2,6-dimethyl-N-(4-methylphenyl)-4-quinolinamine (Compound No. 9 Table I). $[α]_D^{20}$=36° (c=0.28, CH$_2$Cl$_2$).

$^1$H NMR CDCl$_3$: δ 7.17 (1H, s); 7.12–6.98 (4H, m); 6.58 (2H, d); 4.89 (1H, br s); 4.15 (1H, br d); 3.66 (1H, br s); 2.68–2.58 (1H, m); 2.32 (3H, s); 2.27 (3H, s); 2.18 (3H, s); 1.36–1.18 (1H, m); 1.14 (3H, d).

cis-1-Acetyl-6-cyclohexyl-N-(4-clohexylphenyl)-1,2,3,4-tetrahydro-2-methyl-4-quinolinamine (Compound No. 11 Table I).

$^1$H NMR CDCl$_3$: δ 7.21 (1H, s); 7.12–6.98 (4H, m); 6.61 (2H, d); 4.85 (1H, br s); 4.22–4.11 (1H, m); 3.62 (1H, d); 2.68–2.57 (1H, m); 2.54–2.34 (2H, m); 2.17 (3H, s); 1.94–1.12 (24H, m).

cis-1-Acetyl-6-butyl-N-(4-butylphenyl)-1,2,3,4-tetrahydro-2-methyl-4-quinolinamine (Compound No. 12 Table I).

$^1$H NMR CDCl$_3$: δ 7.18 (1H, s); 7.12–6.97 (4H, m); 6.61 (2H, d); 4.88 (1H, br s); 4.22–4.12 (1H, m); 3.68 (1H, br d); 2.70–2.46 (5H, m); 2.18 (3H, s); 1.66–1.49 (4H, m); 1.44–1.12 (8H, m); 1.02–0.86 (6H, m).

cis-1-Acetyl-1,2,3,4-tetrahydro-2-methyl-6-(methylthio)-N-[4-(methylthio)phenyl]-4-quinolinamine (Compound No. 13 Table I).

$^1$H NMR CDCl$_3$: δ 7.23–6.98 (5H, m); 7.57 (2H, d); 4.92–4.74 (1H, m); 4.18–4.10 (1H, m); 3.84 (1H, br d); 2.66–2.57 (1H, m); 2.40 (3H, s); 2.38 (3H, s); 2.15 (3H, s); 1.32–1.18 (1H, m); 1.13 (3H, d).

cis-1,2,3,4-Tetrahydro-2,6-dimethyl-N-(4-methylphenyl)-1-(1-oxopropyl)-4-quinolinamine (Compound No. 15 Table I).

$^1$H NMR CDCl$_3$: δ 7.14 (1H, s); 7.09–6.97 (4H, m); 6.56 (2H, d); 4.96–4.82 (1H, m); 4.11 (1H, dd); 3.64 (1H, br s); 2.66–2.32 (3H, m); 2.31 (3H, s); 2.25 (3H, s); 1.34–1.08 (7H, m).

cis-1-Acetyl-6-azido-N-(4-azidophenyl)-1,2,3,4-tetrahydro-2-methyl-4-quinolinamine (Compound No. 16 Table I).

$^1$H NMR CDCl$_3$: δ 7.18–6.82 (5H, m); 6.61 (2H, d); 4.88 (1H, br s); 4.13 (1H, dd); 3.77 (1H, br s); 2.68–2.60 (1H, m); 2.16 (3H, s); 1.34–1.10 (4H, m).

cis-1-Acetyl-4-[(4-carboxyphenyl)amino]-1,2,3,4-tetrahydro-2-methyl-6-quinolinecarboxylic acid (Compound No. 17 Table I).

$^1$H NMR MeOD (two protons are obscured by the H$_2$O-signal): δ 7.96–7.74 (4H, m); 7.33 (1H, d); 6.68 (2H, d); 4.37 (1H, dd); 2.74–2.62 (1H, m); 2.24–2.13 (3H, m); 1.43–1.23 (1H, m); 1.17 (3H, d).

cis-1-Acetyl-1,2,3,4-tetrahydro-4-[[4-(methoxycarbonyl)phenyl]amino]-2-methyl-6-quinolinecarboxylic acid methyl ester (Compound No. 18 Table I).

$^1$H NMR CDCl$_3$: δ 7.99 (1H, dd); 7.94–7.86 (3H, m); 7.28–7.20 (1H, m); 6.62 (2H, d); 4.94–4.82 (1H, m); 4.37–4.23 (2H, m); 3.85 (6H, s); 2.74–2.64 (1H, m); 2.22 (3H, s); 1.40–1.28 (1H, m); 1.18 (3H, d).

cis-1-Acetyl-N-(2-chlorophenyl)-1,2,3,4-tetrahydro-2-methyl-4-quinolinamine (Compound No. 19 Table I).

$^1$H NMR CDCl$_3$: δ 7.36–7.08 (6H, m); 6.70 (1H, dt); 6.61 (1H, d); 4.95 (1H, br d); 4.51 (1H, d); 4.31–4.22 (1H, m); 2.76–2.66 (1H, m); 2.20 (3H, s); 1.38 (1H, q); 1.19 (3H, d).

cis-1-Acetyl-N-(3chlorophenyl)-1,2,3,4-tetrahydro-2-methyl-4-quinolinamine (Compound No. 20 Table I).

$^1$H NMR CDCl$_3$: δ 7.34–7.07 (5H, m); 6.76–6.70 (1H, m); 6.63 (1H, t); 6.52 (1H, dd); 5.00–4.85 (1H, m); 4.25–4.16 (1H, m); 3.91 (1H, d); 2.71–2.61 (1H, m); 2.20 (3H, s); 1.35–1.22 (1H, m); 1.17 (3H, d).

cis-1-Acetyl-N-(4-chlorophenyl)-1,2,3,4-tetrahydro-2-methyl-4-quinolinamine (Compound No. 21 Table I).

$^1$H NMR CDCl$_3$: δ 7.35–7.07 (6H, m); 6.61–6.53 (2H, m); 5.00–4.84 (1H, m); 4.17 (1H, d); 3.86 (11H, br s); 2.71–2.60 (1H, m); 2.20 (3H, s); 1.35–1.22 (1H, m);. 1.16 (3H, d).

cis-1-Acetyl-N-(4-bromophenyl)-1,2,3,4-tetrahydro-2-methyl-4-quinolinamine (Compound No. 22 Table I).

$^1$H NMR CDCl$_3$: δ 7.34–7.10 (5H, m); 6.89 (1H, br s); 6.53 (2H, d); 5.00–4.85 (1H, m); 4.17 (1H, dd); 2.71–2.60 (1H, m); 2.20 (3H, s); 1.34–1.22 (1H, m); 1.17 (3H, d).

cis-1-Acetyl-1,2,3,4-tetrahydro-N-(4-iodophenyl)-2-methyl-4-quinolinamine (Compound No. 23 Table I).

$^1$H NMR CDCl$_3$: δ 7.45 (2H, d); 7.34–7.10 (4H, m); 6.44 (2H, d); 4.99–4.85 (1H, m); 4.17 (1H, dd); 3.88 (1H, br s); 2.70–2.60 (1H, m); 2.19 (3H, s); 1.34–1.21 (1H, m); 1.16 (3H, d).

cis-1-Acetyl-1,2,3,4-tetrahydro-N-(2-methoxyphenyl)-2-methyl-4-quinolinamine (Compound No. 24 Table I).

$^1$H NMR CDCl$_3$: δ 7.34–7.25 (2H, m); 7.23–7.10 (2H, m); 6.88–6.81 (2H, m); 6.77–6.70 (1H, m); 6.54 (1H, d); 5.00–4.86 (1H, m); 4.47 (1H, br s); 4.21 (1H, dd); 3.92 (3H, s); 2.73–2.64 (1H, m); 2.20 (3H, s); 1.40–1.28 (1H, m); 1.17 (3H, d).

cis-1-Acetyl-1,2,3,4-tetrahydro-N-(4-methoxyphenyl)-2-methyl-4-quinolinamine (Compound No. 25 Table I).
$^1$H NMR CDCl$_3$: δ 7.36–7.09 (4H, m); 6.79 (2H, d); 6.64–6.57 (2H, m); 4.96–4.82 (1H, m); 4.13 (1H, dd); 3.74 (3H, s); 2.68–2.59 (1H, m); 2.17 (3H, s); 1.28–1.10 (4H, m).

cis-1-Acetyl-1,2,3,4-tetrahydro-2-methyl-N-(3-methylphenyl)-4-quinolinamine (Compound No. 26 Table I).
$^1$H NMR CDCl$_3$: δ 7.37–7.03 (5H, m); 6.58 (1H, d); 6.51–6.41 (2H, m); 4.96–4.82 (1H, m); 4.21 (1H, dd); 2.69–2.59 (1H, m); 2.27 (3H, s); 2.18 (3H, s); 1.30–1.19 (1H, m); 1.15 (3H, d).

(2S*,4R*)-1-Acetyl-2-methyl-N-(4-methylphenyl)-1,2,3,4-tetrahydro-4-quinolinamine (Compound No. 27 Table I). [α]$_D^{20}$=183° (c=0.36, CH$_2$Cl$_2$);
$^1$H NMR CDCl$_3$: δ 7.36–7.08 (4H, m); 7.00 (2H, d); 6.56 (2H, d); 4.96–4.82 (1H, m); 4.17 (1H, dd); 2.68–2.59 (1H, m); 2.24 (3H, s); 2.18 (3H, s); 1.30–1.10 (4H, m).

cis-1-Acetyl-N-(2-chloro-4-methylphenyl)-2-methyl-1,2,3,4-tetrahydro-4-quinolinamine (Compound No. 28 Table I).
$^1$H NMR CDCl$_3$: δ 7.32–7.08 (5H, m); 6.90 (1H, dd); 6.50 (1H, d); 4.91 (1H, br d); 4.33 (1H, br s); 4.21 (1H, dd); 2.73–2.63 (1H, m); 2.23 (3H, s); 2.18 (3H, s); 1.40–1.27 (1H, m); 1.16(3H, d).

cis-1-Acetyl-N-(4-chloro-2-methylphenyl)-2-methyl-1,2,3,4-tetrahydro-4-quinolinamine (Compound No. 29 Table I).
$^1$H NMR CDCl$_3$: δ 7.32–6.98 (6H, m); 6.41 (1H, d); 4.92 (1H, br d); 4.25–4.15 (1H, m); 3.63 (1H, br d); 2.72–2.62 (1H, m); 2.21 (3H, s); 2.18 (3H, s); 1.39–1.27 (1H, m); 1.16 (3H, d).

cis-1-Acetyl-N-(2,3-dichlorophenyl)-2-methyl-1,2,3,4-tetrahydro-4-quinolinamine (Compound No. 30 Table I).
$^1$H NMR CDCl$_3$: δ 7.33–7.12 (4H, m); 7.02 (1H, t); 6.84 (1H, dd); 6.48 (1H, d); 4.93 (1H, br s); 4.64 (1H, br d); 4.28–4.20 (1H, m); 2.74–2.65 (1H, m); 2.18 (3H, s); 1.44–1.31 (1H, m); 1.16(3H, d).

cis-1-Acetyl-N-(2,4-dichlorophenyl)-2-methyl-1,2,3,4-tetrahydro-4-quinolinamine (Compound No. 31 Table I).
$^1$H NMR CDCl$_3$: δ 7.34–7.10 (5H, m); 7.06 (1H, dd); 6.50 (1H, d); 4.92 (1H, br s); 4.46 (1H, br d); 4.24–4.16 (1H, m); 2.73–2.64 (1H, m); 2.18 (3H, s); 1.36 (1H, q); 1.16 (3H, d).

cis-1-Acetyl-N-(2,5-dichlorophenyl)-2-methyl-1,2,3,4-tetrahydro-4-quinolinamine (Compound No. 32 Table I).
$^1$H NMR CDCl$_3$: δ 7.34–7.12 (5H, m); 6.65 (1H, dd); 6.55 (1H, d); 4.98–4.86 (1H, m); 4.53 (1H, br d); 4.26–4.17 (1H, m); 2.74–2.64 (1H, m); 2.21 (3H, s); 1.36 (1H, q); 1.17 (3H, d).

cis-1-Acetyl-N-(3,4-dichlorophenyl)-2-methyl-1,2,3,4-tetrahydro-4-quinolinamine (Compound No. 33 Table I).
$^1$H NMR CDCl$_3$: δ 7.33–7.10 (5H, m); 6.70 (1H, d); 6.47 (1H, dd); 4.97–4.84 (1H, m); 4.14 (1H, dd); 2.68–2.58 (1H, m); 2.18 (3H, s); 1.32–1.20 (1H, m); 1.15 (3H, d).

cis-1-Acetyl-N-(3,5-dichlorophenyl)-2-methyl-1,2,3,4-tetrahydro-4-quinolinamine (Compound No. 34 Table I).
$^1$H NMR CDCl$_3$: δ 7.34–7.11 (4H, m); 6.72 (1H, t); 6.49 (2H, d); 4.96–4.84 (1H, m); 4.21–4.12 (1H, m); 4.06–3.96 (1H, m); 2.68–2.58 (1H, m); 2.20 (3H, s); 1.33–1.20 (1H, m); 1.15 (3H, d).

cis-1-Acetyl-N-(4-cyclohexylphenyl)-2-methyl-1,2,3,4-tetrahydro-4-quinolinamine (Compound No. 35 Table I).
$^1$H NMR CDCl$_3$: δ 7.36 (1H, d); 7.30–7.08 (3H, m); 7.03 (2H, d); 6.59 (2H, d); 4.94–4.81 (1H, m); 4.17 (1H, dd); 3.76 (1H, br s); 2.68–2.58 (1H, m); 2.44–2.34 (1H, m); 2.17 (3H, s); 1.90–1.18 (11H, m); 1.14 (3H, d).

cis-1-Acetyl-N-(1,3-benzodioxol-5-yl)-2-methyl-1,2,3,4-tetrahydro-4-quinolinamine (Compound No. 37 Table I).
$^1$H NMR CDCl$_3$: δ 7.37–7.08 (4H, m); 6.65 (1H, d); 6.28 (1H, d); 6.08 (1H, dd); 5.87 (2H, s); 4.89 (1H, br d); 4.30–3.98 (2H, m); 2.68–2.57 (1H, m); 2.18 (3H, s); 1.22 (1H, q); 1.14 (3H, d).

cis-1-Acetyl-6-chloro-2-methyl-N-(4-methylphenyl)-1,2,3,4-tetrahydro-4-quinolinamine (Compound No. 38 Table I).
$^1$H NMR CDCl$_3$: δ 7.34 (1H, s); 7.27–7.22 (1H, m); 7.10–6.97 (3H, m); 6.55 (2H, d); 4.85 (1H, br s); 4.12 (1H, dd); 2.68–2.58 (1H, m); 2.25 (3H, s); 2.16 (3H, s); 1.30–1.18 (1H, m); 1.14 (3H, d).

cis-1-Acetyl-6-chloro-2-methyl-N-[4-(4-morpholinyl)phenyl]-1,2,3,4-tetrahydro-4-quinolinamine (Compound No. 39 Table I).
$^1$H NMR CDCl$_3$: δ 7.28 (1H, s); 7.22–7.16 (1H, m); 7.06–6.96 (1H, m); 6.86–6.73 (2H, m); 6.55 (2H, br d); 4.79 (1H, br s); 4.03 (1H, br d); 3.80 (4H, br s); 2.98 (4H, br s); 2.62–2.52 (1H, m); 2.10 (3H, s); 1.24–1.03 (4H, m).

cis-1-Acetyl-N-(4-methoxyphenyl)-2,6-dimethyl-1,2,3,4-tetrahydro-4-quinolinamine (Compound No. 40 Table I).
$^1$H NMR CDCl$_3$: δ 7.17 (1H, s); 7.11–6.98 (2H, m); 6.81 (2H, d); 6.63 (2H, d); 4.88 (1H, br s); 4.11 (1H, dd); 3.77 (3H, s); 3.54 (1H, br s); 2.68–2.58 (1H, m); 2.34 (3H, s); 2.17 (3H, s); 1.27–1.10 (4H, m).

cis-1-Acetyl-6-chloro-N-(4-methoxyphenyl)-2-methyl-1,2,3,4-tetrahydro-4-quinolinamine (Compound No. 41 Table I).
$^1$H NMR CDCl$_3$: δ 7.34 (1H, d); 7.28–7.22 (1H, m); 7.13–7.01 (1H, m); 6.80 (2H, d); 6.59 (2H, d); 4.84 (1H, br s); 4.07 (1H, dd); 3.75 (3H, s); 2.68–2.58 (1H, m); 2.16 (3H, s); 1.28–1.10 (4H, m).

cis-1-Acetyl-4-[[4-(ethoxycarbonyl)phenyl]amino]-1,2,3,4-tetrahydro-2-methyl-6-quinolinecarboxylic acid ethyl ester (Compound No. 42 Table I).
$^1$H NMR CDCl$_3$: δ 7.99 (1H, dd); 7.94–7.86 (3H, m); 7.23 (1H, d); 6.62 (2H, d); 4.94–4.82 (1H, m); 4.38–4.25 (5H, m); 2.74–2.64 (1H, m); 2.21 (3H, s); 1:39–1.27 (7H, m); 1.17 (3H, d).

cis-4-{[1-Acetyl-2-ethyl-1,2,3,4-tetrahydro-4-quinolinyl]amino}benzonitrile (Compound No. 43 Table I).
$^1$H NMR CDCl$_3$: δ 7.45 (2H, d); 7.31 (1H, dt); 7.23–7.08 (3H, m); 6.60 (2H, d); 4.87 (1H, br s); 4.35 (1H, d); 4.31–4.22 (1H, m); 2.71–2.61 (1H, m); 2.17 (3H, s); 1.64–1.22 (3H, m); 0.86 (3H, t).

cis-1-Acetyl-1,2,3,4-tetrahydro-2-methyl-4-[[4-[(1-methylethoxy)carbonyl]-phenyl]amino]-6-quinolinecarboxylic acid 1-methylethyl ester (Compound No. 44 Table I).
$^1$H NMR CDCl$_3$: δ 7.97 (1H, dd); 7.93–7.86 (3H, m); 7.22 (1H, d); 6.63 (2H, d); 5.24–5.12 (2H, m); 4.94–4.83 (1H, m); 4.34 (1H, dd); 2.74–2.65 (1H, m); 2.20 (3H, s); 1.38–1.23 (13H, m); 1.17 (3H, d).

cis-1-Acetyl-N-(4-chlorophenyl)-6-methoxy-2-methyl-1,2,3,4-tetrahydro-4-quinolinamine (Compound No. 45 Table I).
$^1$H NMR CDCl$_3$: δ 7.19–7.02 (3H, m); 6.88–6.78 (2H, m); 6.58 (2H, br s); 4.93 (1H, br s); 4.13 (1H, dd); 3.75 (3H, s); 2.68–2.58 (1H, m); 2.16 (3H, s); 1.31–1.18 (1H, m); 1.13 (3H, d).

cis-1-Acetyl-6-methoxy-2-methyl-N-(4-methylphenyl)-1,2,3,4-tetrahydro-4-quinolinamine (Compound No. 46 Table I).

$^1$H NMR CDCl$_3$: δ 7.10–6.92 (4H, m); 6.80 (1H, dd); 6.64 (2H, br s); 4.90 (1H, br s); 4.16 (1H, dd); 3.75 (3H, s); 2.68–2.58 (1H, m); 2.26 (3H, s); 2.15 (3H, s); 1.30–1.17 (1H, m); 1.12 (3H, d).

cis-4-{[1-Acetyl-6-methoxy-2-methyl-1,2,3,4-tetrahydro-4-quinolinyl]amino}-phenyl)(phenyl)methanone (Compound No. 47 Table I).

$^1$H NMR CDCl$_3$: δ 7.80–7.71 (4H, m); 7.57–7.42 (3H, m); 7.09 (1H, br d); 6.86–6.79 (2H, m); 6.66 (2H, d); 4.97 (1H, br s); 4.30 (1H, dd); 3.75 (3H, s); 2.73–2.63 (1H, m); 2.17 (3H, s); 1.38–1.23 (1H, m); 1.16 (3H, d).

cis-4-{[1-Acetyl-6-chloro-1,2,3,4-tetrahydro-2-methyl-4-quinolinyl]amino}benzoic acid methyl ester (Compound No. 48 Table I).

$^1$H NMR CDCl$_3$: δ 7.89 (2H, d); 7.30–7.17 (2H, m); 7.10 (1H, br d); 6.59 (2H, d); 4.89 (1H, br s); 4.29–4.18 (2H, m); 3.86 (3H, s); 2.71–2.62 (1H, m); 2.18 (3H, s); 1.38–1.24 (1H, m); 1.15 (3H, d).

cis-1-(4-{[1-Acetyl-6-methoxy-2-methyl-1,2,3,4-tetrahydro-4-quinolinyl]amino}-phenyl)ethanone (Compound No. 49 Table I).

$^1$H NMR CDCl$_3$: δ 7.86 (2H, d); 7.08 (1H, br d); 6.86–6.75 (2H, m); 6.63 (2H, d); 4.96 (1H, br s); 4.29 (1H, dd); 3.74 (3H, s); 2.71–2.62 (1H, m); 2.52 (3H, s); 2.18 (3H, s); 1.36–1.23 (1H, m); 1.15 (3H, d).

cis-4-{[1-Acetyl-6-methoxy-2-methyl-1,2,3,4-tetrahydro-4-quinolinyl]amino}-benzamide (Compound No. 50 Table I).

$^1$H NMR CDCl$_3$: δ 7.70 (2H, d); 7.08 (1H, br d); 6.86–6.76 (2H, m); 6.64 (2H, d); 6.18 (2H, br s); 4.96 (1H, br s); 4.26 (1H, dd); 3.74 (3H, s); 2.70–2.61 (1H, m); 2.18 (3H, s); 1.35–1.21 (1H, m); 1.15 (3H, d).

cis-4-{[1-Acetyl-6-methoxy-2-methyl-1,2,3,4-tetrahydro-4-quinolinyl]amino}-benzonitrile (Compound No. 51 Table I).

$^1$H NMR CDCl$_3$: δ 7.45 (2H, d); 7.14–7.03 (1H, m); 6.81 (1H, dd); 6.71 (1H, d); 6.61 (2H, d); 4.94 (1H, br s); 4.32–4.16 (2H, m); 3.73 (3H, s); 2.68–2.59 (1H, m); 2.16 (3H, s); 1.34–1.22 (1H, m); 1.14 (3H, d).

cis-4-[{1-Acetyl-1,2,3,4-tetrahydro-6-methoxy-2-methyl-4-quinolinyl}amino]-benzoic acid methyl ester (Compound No. 52 Table I).

$^1$H NMR CDCl$_3$: δ 7.86 (2H, d); 7.05 (1H, br d); 6.82–6.73 (2H, m); 6.60 (2H, d); 4.93 (1H, br s); 4.40–4.18 (2H, m); 3.84 (3H, s); 3.70 (3H, s); 2.68–2.58 (1H, m); 2.15 (3H, s); 1.32–1.19 (1H, m); 1.13 (3H, d).

cis-4-{[1-Acetyl-2,8-dimethyl-1,2,3,4-tetrahydro-4-quinolinyl]amino}benzonitrile (Compound No. 53 Table I).

$^1$H NMR CDCl$_3$: δ 7.44 (2H, d); 7.27–7.12 (2H, m); 7.00 (1H, d); 6.58 (2H, d); 5.23–5.12 (1H, m); 4.33 (1H, br d); 4.19–4.10 (1H, m); 2.72–2.63 (1H, m); 2.27 (3H, s); 1.95 (3H, s); 1.21–1.13 (1H, m); 1.06 (3H, d).

cis-1-Acetyl-6-methoxy-2-methyl-N-[4-(4-morpholinyl)phenyl]-1,2,3,4-tetrahydro-4-quinolinamine (Compound No. 54 Table I).

$^1$H NMR CDCl$_3$: δ 7.04 (1H, br d); 6.94–6.76 (4H, m); 6.64 (2H, d); 4.90 (1H, br s); 4.18–4.07 (1H, m); 3.90–3.81 (5H, m); 3.75 (3H, s); 3.10–2.94 (4H, m); 2.68–2.57 (1H, m); 2.15 (3H, s); 1.24–1.08 (4H, m).

cis-2-{[1-Acetyl-6-chloro-2-methyl-1,2,3,4-tetrahydro-4-quinolinyl]amino}-benzamide (Compound No. 55 Table I).

$^1$H NMR CDCl$_3$: δ 8.24 (1H, d); 7.46 (1H, dd); 7.34–7.20 (3H, m); 7.08 (1H, br s); 6.67 (1H, t); 6.56 (1H, d); 5.84 (2H, br s); 4.88 (1H, br s); 4.23–4.14 (1H, m); 2.73–2.64 (1H, m); 2.18 (3H, s); 1.47–1.33 (1H, m); 1.15 (3H, d).

cis-4-{[1-Acetyl-2-methyl-1,2,3,4-tetrahydro-4-quinolinyl]amino}benzamide (Compound No. 56 Table I).

$^1$H NMR CDCl$_3$: δ 7.69 (2H, d); 7.34–7.13 (4H, m); 6.64 (2H, d); 5.93 (2H, br s); 4.95 (1H, br d); 4.34–4.22 (2H, m); 2.73–2.64 (1H, m); 2.21 (3H, s); 1.32 (1H, q); 1.18 (3H, d).

cis-4-{[1-Acetyl-2,6-dimethyl-1,2,3,4-tetrahydro-4-quinolinyl]amino}benzonitrile (Compound No. 57 Table I).

$^1$H NMR CDCl$_3$: δ 7.47 (2H, d); 7.16–6.93 (3H, m); 6.63 (2H, d); 4.93 (1H, br s); 4.33–4.19 (2H, m); 2.70–2.60 (1H, m); 2.32 (3H, s); 2.18 (3H, s); 1.31 (1H, q); 1.16 (3H, d).

cis-1-Acetyl-1,2,3,4-tetrahydro-2,6-dimethyl-N-[4-(4-morpholinyl)phenyl]-4-quinolinamine (Compound No. 58 Table I).

$^1$H NMR CDCl$_3$: δ 7.17 (1H, s); 7.11–6.99 (2H, m); 6.86 (2H, d); 6.64 (2H, d); 4.89 (1H, br s); 4.13 (1H, dd); 3.86 (4H, t); 3.57 (1H, br s); 3.05 (4H, t); 2.68–2.58 (1H, m); 2.32 (3H, s); 2.16 (3H, s); 1.29–1.10 (4H, m).

cis-2-{[1-Acetyl-2-methyl-1,2,3,4-tetrahydro-4-quinolinyl]amino}benzamide (Compound No. 59 Table I).

$^1$H NMR CDCl$_3$: δ 8.27 (1H, d); 7.44 (1H, d); 7.34–7.06 (4H, m); 6.70–6.59 (2H, m); 5.73 (2H, br s); 4.92 (1H, br s); 4.31–4.21 (1H, m); 2.75–2.65 (1H, m); 2.18 (3H, s); 1.38 (1H, q); 1.15 (3H, d).

cis-N-(4-{[1-Acetyl-2-methyl-1,2,3,4-tetrahydro-4-quinolinyl]amino}phenyl)-acetamide (Compound No. 60 Table I).

$^1$H NMR CDCl$_3$: δ 7.32–7.08 (5H, m); 7.02–6.90 (1H, br s); 6.59 (2H, d); 4.90 (1H, br d); 4.17 (1H, br d); 3.76 (1H, br s); 2.70–2.59 (1H, m); 2.18 (3H, s); 2.13 (3H, s); 1.32–1.10 (4H, m).

cis-N-(4-{[1-Acetyl-6chloro-2-methyl-1,2,3,4-tetrahydro-4-quinolinyl]amino}-phenyl)acetamide (Compound No. 61 Table I).

$^1$H NMR CDCl$_3$: δ 7.33–6.91 (5H, m); 6.63–6.54 (2H, d); 4.86 (1H, br s); 4.12 (1H, br d); 3.71 (1H, br s); 2.69–2.59 (1H, m); 2.17 (3H, s); 2.14 (3H, s); 1.32–1.09 (4H, m).

cis-4-[{1-Acetyl-1,2,3,4-tetrahydro-2-methyl-4-quinolinyl}amino]-benzoic acid methyl ester (Compound No. 62 Table I).

$^1$H NMR CDCl$_3$: δ 7.88 (2H, d); 7.33–7.12 (4H, m); 6.60 (2H, d); 4.93 (1H, br d); 4.34–4.20 (2H, m); 3.85 (3H, s); 2.72–2.63 (1H, m); 2.19 (3H, s); 1.31 (1H, q); 1.16 (3H, d).

cis-N-(4-{[1-Acetyl-6-methoxy-2-methyl-1,2,3,4-tetrahydro-4-quinolinyl]amino}-phenyl)acetamide (Compound No. 63 Table I).

$^1$H NMR CDCl$_3$: δ 7.33–7.25 (2H, m); 7.12–6.77 (4H, m); 6.61 (2H, d); 4.92 (1H, br s); 4.15 (1H, dd); 3.75 (3H, s); 2.69–2.59 (1H, m); 2.16 (6H, s); 1.30–1.07 (4H, m).

cis-1-Acetyl-1,2,3,4-tetrahydro-6-methoxy-2-methyl-N-[4-(methylsulfonyl)phenyl]-4-quinolinamine (Compound No. 64 Table I).

$^1$H NMR CDCl$_3$: δ 7.73 (2H, d); 7.08 (1H, br d); 6.82 (1H, dd); 6.73 (1H, br d); 6.67 (2H, d); 4.95 (1H, br s); 4.36–4.20 (2H, m); 3.74 (3H, s); 3.01 (3H, s); 2.69–2.60 (1H, m); 2.17 (3H, s); 1.36–1.22 (1H, m); 1.14 (3H, d).

1-[(2S*,4R*)-4-(4-benzoylanilino)-6-bromo-2-methyl-3,4-dihydro-1(2H)-quinolinyl]-1-ethanone (Compound No. 65 Table I). $[\alpha]_D^{20}=132°$ (c=0.8, $CH_2Cl_2$).

$^1$H NMR MeOD (two protons is obscured by the $H_2O$-signal): δ 7.73–7.64 (4H, m); 7.60–7.44 (4H, m); 7.31 (1H, dd); 7.24 (1H, br d); 6.73 (2H, d); 4.39 (1H, dd); 2.72–2.63 (1H, m); 2.19 (3H, s); 1.43–1.30 (1H, m); 1.16 (3H, d).

cis-1-Acetyl-1,2,3,4-tetrahydro-N-(4-methoxyphenyl)-2-methyl-6-(4-morpholinyl)-4-quinolinamine (Compound No. 66 Table I).

$^1$H NMR $CDCl_3$: δ 7.03 (1H, br d); 6.96 (1H, br d); 6.83–6.76 (3H, m); 6.63 (2H, d); 4.88 (1H, br s); 4.10 (1H, dd); 3.83 (4H, t); 3.77 (3H, s); 3.51 (1H, br s); 3.17–3.04 (4H, m); 2.66–2.58 (1H, m); 2.16 (3H, s); 1.26–1.11 (4H, m).

cis-4-{[1-Acetyl-2-methyl-6-(4-morpholinyl)-1,2,3,4-tetrahydro-4-quinolinyl]-amino}benzonitrile (Compound No. 67 Table I).

$^1$H NMR $CDCl_3$: δ 7.45 (2H, d); 7.09 (1H, br d); 6.86 (1H, dd); 6.78 (1H, br s); 6.63 (2H, d); 4.91 (1H, br s); 4.27–3.92 (2H, m); 3.83 (4H, t); 3.16–3.01 (4H, m); 2.68–2.58 (1H, m); 2.18 (3H, s); 1.30 (1H, q); 1.14(3H, d).

cis-1-Acetyl-1,2,3,4-tetrahydro-2-methyl-6-(4-morpholinyl)-N-phenyl-4-quinolinamine (Compound No. 68 Table I).

$^1$H NMR $CDCl_3$: δ 7.25–6.64 (8H, m); 4.90 (1H, br s); 4.19 (1H, dd); 3.82 (4H, t); 3.19–3.02 (4H, m); 2.67 (1H, m); 2.17 (3H, s); 1.33–1.10 (4H, m).

cis-4-[{1-Acetyl-2-ethyl-1,2,3,4-tetrahydro-4-quinolinyl}amino]-benzoic acid methyl ester (Compound No. 69 Table I).

$^1$H NMR $CDCl_3$: δ 7.88 (2H, d); 7.32–7.07 (4H, m); 6.59 (2H, d); 4.86 (1H, br s); 4.30 (1H, dd); 3.85 (3H, s); 2.72–2.62(1H, m); 2.18 (3H, s); 1.74–1.26 (3H, m); 0.86 (3H, t).

cis-1-Acetyl-1,2,3,4-tetrahydro-N,2-diphenyl-4-quinolinamine (Compound No. 70 Table I).

$^1$H NMR $CDCl_3$: δ 7.43–7.14 (11H, m); 6.80 (1H, t); 6.70 (2H, d); 5.81 (1H, br s); 4.42 (1H, dd); 3.85 (1H, br s); 2.93–2.84 (1H, m); 2.23 (3H, s); 1.78 (1H, q).

cis-1-Acetyl-1,2,3,4-tetrahydro-2-methyl-6-(methylthio)-N-phenyl-4-quinolinamine (Compound No. 72 Table I).

$^1$H NMR $CDCl_3$: δ 7.30–6.99 (5H, m); 6.76 (1H, t); 6.64 (2H, d); 4.87 (1H, br s); 4.24–4.12 (1H, m); 3.75 (1H, br d); 2.70–2.58 (1H, m); 2.38 (3H, s); 2.16 (3H, s); 1.33–1.05 (4H, m).

cis-1-Acetyl-1,2,3,4-tetrahydro-2-methyl-6-(methylsulfonyl)-N-phenyl-4-quinolinamine (Compound No. 73 Table I).

$^1$H NMR $CDCl_3$: δ 7.96–7.88 (2H, m); 7.39 (1H, d); 7.22 (2H, t); 6.80 (1H, t); 6.65 (2H, d); 4.90–4.78 (1H, m); 4.32–4.23 (1H, m); 3.83 (1H, br d); 3.03 (3H, s); 2.79–2.69 (1H, m); 2.26 (3H, s); 1.41–1.29 (1H, m); 1.21 (3H, d).

(2S*,4R*)-1-Acetyl-1,2,3,4-tetrahydro-6-iodo-2-methyl-N-phenyl-4-quinolinamine (Compound No. 74 Table I). $[\alpha]_D^{20}=309°$ (c=0.6, $CH_3Cl$).

$^1$H NMR $CDCl_3$: δ 7.67 (1H, br d); 7.23 (2H, dt); 6.90 (1H, br d); 7.63 (1H, t); 6.64 (2H, d); 4.86 (1H, br d); 4.17 (1H, br d); 3.74 (1H, br s); 2.69–2.59 (1H, m); 2.19 (3H, s); 1.35–1.22 (1H, m); 1.16 (3H, d).

(2S,4R)-1-Acetyl-6-bromo-2-methyl-N-phenyl-1,2,3,4-tetrahydro-4-quinolinamine (Compound No. 75 Table I). $[\alpha]_D^{20}=278°$ (c=0.11, $CH_2Cl_2$).

$^1$H NMR $CDCl_3$: δ 7.48 (1H, m); 7.43 (1H, d); 7.28–7.18 (2H, m), 7.08–6.98 (1H, d); 6.79 (1H, t); 6.64 (2H, d); 4.92–4.80 (1H, s); 4.18 (1H, dd); 3.90–3.70 (1H, s); 2.71–2.60 (1H, m); 2.18 (3H, s); 1.32–1.19 (1H, m); 1.17 (3H, d).

trans-1-Acetyl-1,2,3,4-tetrahydro-2-methyl-N-phenyl-4-quinolinamine (Compound No. 1 Table II).

$^1$H NMR $CDCl_3$: δ 7.41 (1H, dd); 7.32–7.12 (5H, m); 6.74–6.62 (3H, m); 4.92 (1H, d); 4.61 (1H, d); 3.85 (1H, s); 2.56–2.46 (1H, m); 2.18 (3H, s); 1.81–1.72 (1H, m); 1.20 (3H, d).

trans-1-Acetyl-1,2,3,4-tetrahydro-4-[[4-(methoxycarbonyl)phenyl]amino]-2-methyl-6-quinolinecarboxylic acid methyl ester (Compound No. 18 Table II).

$^1$H NMR $CDCl_3$: δ 8.10 (1H, d); 7.98 (1H, dd); 7.86 (2H, d); 7.37 (1H, d); 6.62 (2H, d); 4.92–4.84 (1H, m); 4.76–4.71 (1H, t); 4.40–4.30 (1H, s br); 3.91 (3H, s); 3.84 (3H, s); 2.50–2.42 (1H, m); 2.21 (3H, s); 1.96–1.88 (1H, m); 1.22 (3H, d).

trans-1-Acetyl-N-(2-chlorophenyl)-2-methyl-1,2,3,4-tetrahydro-4-quinolinamine (Compound No. 21 Table II).

$^1$H NMR $CDCl_3$: δ 7.45–7.18 (6H, m), 6.86 (1H, d); 6.62 (1H, dd); 4.99–4.92 (1H, m); 4.76–4.60 (2H, m); 2.65–2.58 (1H, m); 2.20 (3H, s); 1.81–1.76 (1H, m); 1.01 (3H, d).

trans-1-Acetyl-N-(4-bromophenyl)-1,2,3,4-tetrahydro-2-methyl-4-quinolinamine (Compound No. 24 Table II).

$^1$H NMR $CDCl_3$: δ 7.42 (6H, m); 6.53 (2H, d); 5.0–4.85 (1H, d br); 4.55 (1H, t); 2.58–2.49 (1H, m); 2.18 (3H, s); 1.80–1.72 (1H, m); 1.19 (3H, d).

cis-1-Acetyl-1,2,3,4-tetrahydro-2-methyl-N-(2-pyrazinyl)-4-quinolinamine (Compound No. 1 Table III).

$^1$H NMR $CDCl_3$: δ 8.05–7.99 (2H, m); 7.92 (1H, d); 7.38–7.15 (4H, m); 5.01–4.90 (1H, m); 4.90–4.82 (1H, m); 4.72 (1H, d); 2.73–2.62 (1H, m); 2.18 (3H, s); 1.38–1.25 (1H, m); 1.19 (3H, d).

cis-1-Acetyl-6-chloro-1,2,3,4-tetrahydro-2-methyl-N-(2-pyrazinyl)-4-quinolinamine (Compound No. 2 Table III).

$^1$H NMR $CDCl_3$: δ 8.04–8.01 (2H, m); 7.93 (1H, d); 7.28 (1H, dd); 7.23 (1H, dd); 7.11 (1H, d); 4.98–4.80 (2H, m); 4.80–4.78 (1H, m); 2.70 cis-1-Acetyl-1,2,3,4-tetrahydro-2-methyl-N-(4-pyridinyl)-4-quinolinamine (Compound No. 3 Table III).

–2.62 (1H, m); 2.18 (3H, s); 1.39–1.24 (1H, m); 1.19 (3H, d).

$^1$H NMR $CD_3OD$: δ 8.27 (2H, d); 7.48–7.45 (2H, m); 7.38–7.29 (1H, m); 7.00 (2H, d); 6.61 (1H, d); 5.41 (1H, dd); 5.02–4.88 (1H, m); 2.93–2.82 (1H, m); 2.21 (3H, s); 2.18–2.00 (1H, m); 1.35 (3H, d).

BIOLOGICAL ASSAY

The ability of the compounds described herein to inhibit STAT6 signaling pathway is manifested in their ability to inhibit STAT6 driven reporter gene activity.

The cytokine-responsive human cell line U937 were transfected with a reporter gene plasmid consisting of an interluekin 4 (IL-4) responsive promoter driving the heterologous firefly gene for luciferase. The reporter gene plasmid also contained a gene for neomycin resistance. The IL-4 responsive promoter were constructed by four oligomerized combined C/BEPβ and STAT6 binding sites with the nucleotide sequence GTTGCTCAATCGACTTCCCAAGAA in close contact with a TATA-box. Cells with a stable integration of the reporter gene plasmid were selected by cultivation in neomycin. Such transfected cells were used for IL-4 induction by adding 10 ng/ml recombinant human IL-4 to 0.5–1×$10^6$ cells per ml. IL-4 induction were carried out for 4–5 h. Thereafter the cells were lysed and luciferase activity determined by using standard techniques. Numbers measured are the mean fold induction (fold induction for U937 is defined as the luciferase response in an IL-4 treated U937 cell sample divided by the luciferase response in an untreated U937 cell sample). Typically, IL-4 stimulation gave 15–20 fold induction of the luciferase response. Compounds were added 5 min before IL-4 when tested in the reporter gene assay. Compound effect was expressed as the concentration of compound giving 50 percent inhibition (IC50) of the luciferase response to addition of IL-4. The results from compound testing are shown in Table IV.

TABLE IV

| Inhibition of STAT6-driven reporter gene activity | | | |
|---|---|---|---|
| Compound | No 27 Table I | No 36 Table I | No 74 Table I |
| IC50 μM | 0.80 | 0.43 | 0.18 |

SCHEME 1

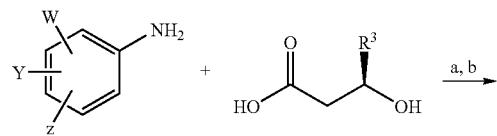

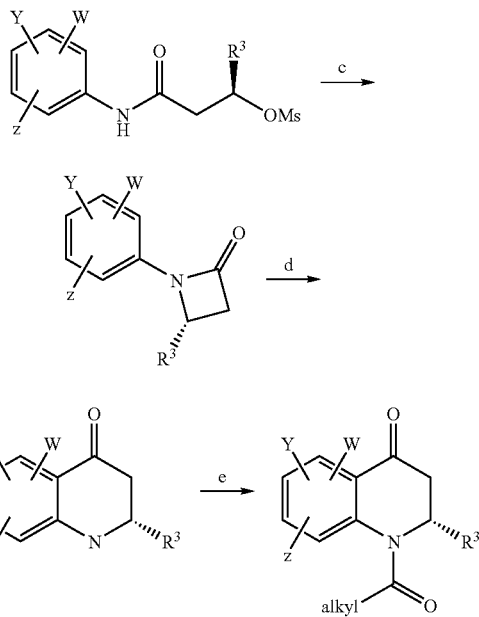

a: N,N dicyclohexyl carbodiimide (DCC), dimethylamino pyridine (DMAP), CH$_2$Cl$_2$, 60%;
b: Ms$_2$O, EtNiPr$_2$, CH$_2$Cl$_2$, 0° C., 80–90%;
c: NaH, DMF, CH$_2$Cl$_2$, 70%;
d: F$_3$CCO$_2$H, 70° C., 75%;
e: (alkyl)COCl, Et$_3$N, CH$_2$Cl$_2$, 50–60%.

SCHEME 2

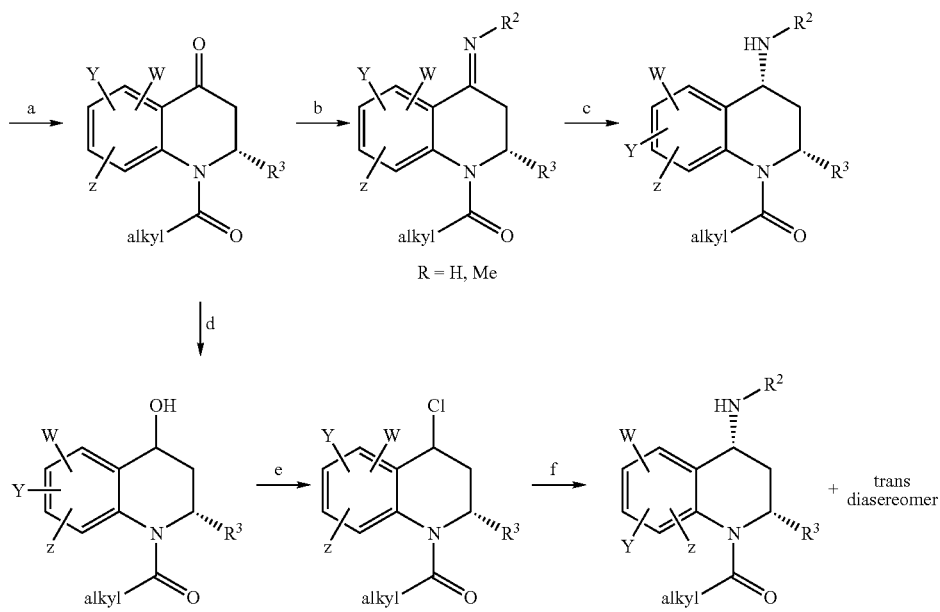

a: (alkyl)COCl, Et$_3$N, CH$_2$Cl$_2$, r.t.;
b: R$^2$NH$_2$, pTSA, molecular sieve 3Å, Toluene, reflux;
c: H$_2$ (1 atmosphere), Pd/C, EtOAc;
d: NaBH$_4$, MeOH, 0° C.;
e: SOCl$_2$, Pyridine, CH$_2$Cl$_2$, 0° C.;
f: R$^2$NH$_2$, MeCN, 80° C.

The invention claimed is:

1. compound of formula (I):

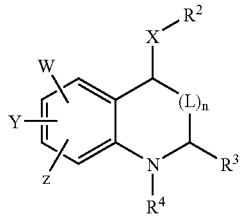

wherein:
L is $CH_2$, O or S;
n is 0 or 1;
W, Y and Z are, independently hydrogen, cyano, nitro, halogen, $N_3$, $C_{1-6}$ alkyl, $C_{1-6}$ alkoxy, $C_{1-6}$ haloalkyl, $C_{1-6}$ haloalkoxy, $C_{1-6}$ alkylthio, $C_{3-6}$ cycloalkyl, $CO_2H$, $CO_2(C_{1-6}$ alkyl), $CONR^5R^6$, $COR^{10}$ $SO_2R^{12}$, methylenedioxy, $NHCOR^{11}$ or heterocyclyl;
$R^2$ is aryl or heteroaryl optionally substituted by cyano, nitro, halogen, $N_3$, $C_{1-6}$ alkyl, $C_{1-6}$ alkoxy, $C_{1-6}$ haloalkyl, $C_{1-6}$ haloalkoxy, $C_{1-6}$ alkylthio, $C_{3-6}$ cycloalkyl, $CO_2H$, $CO_2(C_{1-6}$ alkyl), $CONR^{13}R^{14}$, $COR^{15}$, $SO_2R^{16}$, methylenedioxy, $NHCOR^{17}$ or heterocyclyl;
$R^3$ is $C_{1-4}$ alkyl or $C_{1-4}$ haloalkyl;
$R^4$ is $CO(C_{1-4}$ alkyl) or $CO(C_{1-4}$ haloalkyl);
X is O, S, SO, $SO_2$, $CR^7R^8$ or $NR^9$;
$R^5$, $R^6$, $R^7$, $R^8$, $R^{13}$ and $R^{14}$ are, independently, hydrogen or $C_{1-6}$ alkyl;
$R^9$ is hydrogen, $C_{1-6}$ alkyl or $CO(C_{1-4}$ alkyl);
$R^{10}$, $R^{11}$, $R^{12}$, $R^{15}$, $R^{16}$ and $R^{17}$ are, independently, $C_{1-6}$ alkyl or phenyl;
or a pharmaceutically acceptable salt thereof; or a solvate thereof; provided that the compound of formula (I) is not a compound of formula (Iz):

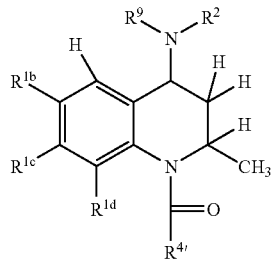

wherein

| $R^{1b}$ | $R^{1d}$ | $R^{1c}$ | $R^{4'}$ | $R^2$ | $R^9$ |
|---|---|---|---|---|---|
| H | H | H | n-butyl | $C_6H_5$ | H |
| H | H | H | n-propyl | $C_6H_5$ | $COCH_3$ |
| H | H | H | n-propyl | $C_6H_5$ | H |
| H | H | H | Ethyl | $C_6H_5$ | H |
| Br | H | H | Methyl | $C_6H_5$ | $COCH_3$ |
| Methyl | H | H | Methyl | 4-$CH_3$—$C_6H_4$ | H |
| Methyl | Methyl | H | Methyl | 2,4-$(CH_3)_2$—$C_6H_3$ | H |
| H | H | H | Methyl | $C_6H_5$ | H |
| $NO_2$ | H | H | Methyl | 4-$NO_2$—$C_6H_4$ | $COCH_3$ |
| $NO_2$ | H | H | Methyl | $C_6H_5$ | $COCH_3$ |
| Cl | H | H | Methyl | $C_6H_5$ | $COCH_3$ |

-continued

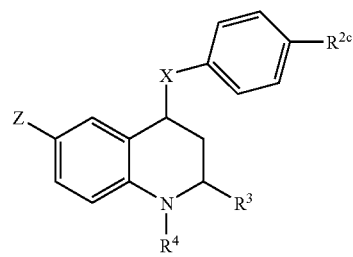

wherein

| $R^{1b}$ | $R^{1d}$ | $R^{1c}$ | $R^{4'}$ | $R^2$ | $R^9$ |
|---|---|---|---|---|---|
| H | H | H | Methyl | $C_6H_5$ | $COCH_3$ |
| H | H | H | Methyl | 2,4-$Br_2$—$C_6H_3$ | $COCH_3$ | in free base or unsolvated form.

2. A compound of formula (Ia):

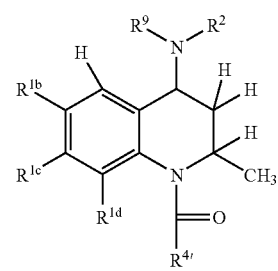

wherein Z, $R^3$, $R^4$ and X are as defined in claim 1, and $R^{2c}$ is hydrogen, cyano, nitro, halogen, $N_3$, $C_{1-6}$ alkyl, $C_{1-6}$ alkoxy, $C_{1-6}$ haloalkyl, $C_{1-6}$ haloalkoxy, $C_{1-6}$ alkylthio, $C_{3-6}$ cycloalkyl, $CO_2H$, $CO_2(C_{1-6}$ alkyl), $CONR^{13}R^{14}$, $COR^{15}$, $SO_2R^{16}$, methylenedioxy, $NHCOR^{17}$ or heterocyclyl; wherein $R^{13}$, $R^{14}$, $R^{15}$, $R^{16}$ and $R^{17}$ are as defined in claim 1; or a pharmaceutically acceptable salt thereof; or a solvate thereof.

3. A compound as claimed in claim 1 wherein X is NH.

4. A compound as claimed in claim 1 wherein $R^3$ is methyl.

5. A compound as claimed in claim 1 wherein $R^4$ is $C(O)CH_3$.

6. A compound as claimed in claim 1 wherein $R^2$ is phenyl para-substituted by $C(O)_2CH_3$, iodo, $N_3$, bromo, methyl, $C(O)_2CH_2CH_3$, cyano or methoxy.

7. Processes for the preparation of a compound of formula (I) as claimed in claim 1 by reacting a compound of formula (II):

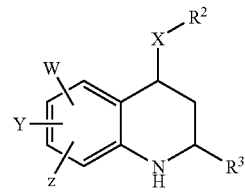

with acetic anhydride in the presence of a base at room temperature.

8. A pharmaceutical composition which comprises a compound of the formula (I) as claimed in claim 1, or a pharmaceutically acceptable salt thereof or solvate thereof, and a pharmaceutically acceptable adjuvant, diluent or carrier.

9. A compound as claimed in claim 1, wherein X is NH; $R^3$ is methyl; and $R^4$ is $C(O)CH_3$.

10. A compound as claimed in claim 9, wherein $R^2$ is phenyl para-substituted by $C(O)_2CH_3$, iodo, $N_3$, bromo, methyl, $C(O)_2CH_2CH_3$, cyano or methoxy.

11. A pharmaceutical composition as claimed in claim 8, wherein the compound is of the formula (I) as claimed in claim 10, or a pharmaceutically acceptable salt thereof of solvate thereof.

12. A pharmaceutical composition as claimed in claim 8, wherein the compound is of the formula (I) as claimed in claim 10, or a pharmaceutically acceptable salt thereof of solvate thereof.

13. A compound as claimed in claim 1, wherein the compound is a compound of Table I, Table II, or Table III.

14. A method for making a pharmaceutical composition as claimed in claim 8, comprising mixing a compound of formula (I) as claimed in claim 1 with a pharmaceutically acceptable adjuvant, diluent or carrier.

* * * * *